(12) United States Patent
Frampton, IV

(10) Patent No.: US 11,299,630 B2
(45) Date of Patent: Apr. 12, 2022

(54) TEMPLATED ASSEMBLY OF COLLAGEN FIBERS AND USES THEREOF

(71) Applicant: 3DBIOFIBR INC., Halifax (CA)

(72) Inventor: John Paul Frampton, IV, Halifax (CA)

(73) Assignee: 3DBIOFIBR INC., Halifax (CA)

( * ) Notice: Subject to any disclaimer, the term of this patent is extended or adjusted under 35 U.S.C. 154(b) by 183 days.

(21) Appl. No.: 16/480,202

(22) PCT Filed: Jan. 26, 2018

(86) PCT No.: PCT/CA2018/050097
§ 371 (c)(1),
(2) Date: Jul. 23, 2019

(87) PCT Pub. No.: WO2018/137041
PCT Pub. Date: Aug. 2, 2018

(65) Prior Publication Data
US 2019/0367733 A1    Dec. 5, 2019

Related U.S. Application Data

(60) Provisional application No. 62/450,828, filed on Jan. 26, 2017.

(51) Int. Cl.
| | | |
|---|---|---|
| *C08L 89/06* | (2006.01) | |
| *A61L 15/22* | (2006.01) | |
| *A61L 15/42* | (2006.01) | |
| *A61L 15/44* | (2006.01) | |
| *A61L 15/60* | (2006.01) | |
| *A61L 15/64* | (2006.01) | |
| *A61L 27/16* | (2006.01) | |
| *A61L 27/20* | (2006.01) | |
| *A61L 27/24* | (2006.01) | |
| *A61L 27/26* | (2006.01) | |
| *A61L 27/52* | (2006.01) | |
| *A61L 27/54* | (2006.01) | |
| *A61L 27/56* | (2006.01) | |
| *A61L 27/58* | (2006.01) | |
| *C08L 5/02* | (2006.01) | |
| *C12M 3/00* | (2006.01) | |
| *C12M 1/12* | (2006.01) | |
| *D01D 5/00* | (2006.01) | |
| *D01F 4/00* | (2006.01) | |

(52) U.S. Cl.
CPC ............. *C08L 89/06* (2013.01); *A61L 15/225* (2013.01); *A61L 15/425* (2013.01); *A61L 15/44* (2013.01); *A61L 15/60* (2013.01); *A61L 15/64* (2013.01); *A61L 27/16* (2013.01); *A61L 27/20* (2013.01); *A61L 27/24* (2013.01); *A61L 27/26* (2013.01); *A61L 27/52* (2013.01); *A61L 27/54* (2013.01); *A61L 27/56* (2013.01); *A61L 27/58* (2013.01); *C08L 5/02* (2013.01); *C12M 21/08* (2013.01); *C12M 25/14* (2013.01); *D01D 5/00* (2013.01); *D01F 4/00* (2013.01); *A61L 2300/412* (2013.01); *A61L 2430/34* (2013.01); *C08L 2201/06* (2013.01); *C08L 2203/02* (2013.01); *C08L 2203/12* (2013.01)

(58) Field of Classification Search
CPC ...... A61L 15/225; A61L 15/425; A61L 15/44; A61L 15/60; A61L 15/64; A61L 27/16; A61L 27/20; A61L 27/24; A61L 27/26; A61L 27/50; A61L 27/3826; A61L 27/48; A61L 27/3804; A61L 27/52; A61L 27/54; A61L 27/56; A61L 27/58; A61L 2300/412; A61L 2430/34; A61L 2430/30; C08L 89/06; C08L 5/02; C08L 2201/06; C08L 2203/02; C08L 2203/12; C12M 21/08; C12M 25/14; D01D 5/00; D01F 4/00; D01F 9/00; D06M 2101/14; D06M 15/03; D06M 15/285; C07K 14/78
See application file for complete search history.

(56) References Cited

U.S. PATENT DOCUMENTS

| | | | | |
|---|---|---|---|---|
| 2004/0001878 A1* | 1/2004 | DeBusk | ................. | A61L 15/44 424/445 |
| 2011/0150973 A1* | 6/2011 | Bowlin | ................. | A61L 15/28 424/447 |

FOREIGN PATENT DOCUMENTS

| | | | |
|---|---|---|---|
| CA | 2 479 903 A1 | 10/2003 | |
| WO | 2013/172788 A1 | 11/2013 | |
| WO | 2015/102980 A1 | 7/2015 | |
| WO | WO-2016025945 A1 * | 2/2016 | ............. A61L 27/18 |

OTHER PUBLICATIONS

Frampton, J.P., et al.; Advanced Healthcare Materials, 2014, vol. 4, p. 313-324.*
NIH; Composition of the Blood, p. 1-3, retrieved Jul. 22, 2021.*
PCT International Search Report, PCT/CA2018/050097, dated Apr. 18, 2018 (5 pages).
Frampton et al., "Elongation of Fibers from Highly Viscous Dextran Solutions Enables Fabrication of Rapidly Dissolving Drug Carrying Fabrics", Adv, Healthcare Mater,, 4(313-319), 2015.
Liu et al., "Templated Assembly of Collagen Fibers Directs Growth in 2D and 3D", Scientific Reports, 7(9628):1-9, 2017.
Extended European Search Report dated Sep. 14, 2020 on EP 18745077.
Nam E, et al. Macromol. Biosci. 2016, 16, 995-1000.

* cited by examiner

*Primary Examiner* — Robert S Jones, Jr.
(74) *Attorney, Agent, or Firm* — Brunet & Co. Ltd.; Robert Brunet; Hans Koenig

(57) ABSTRACT

The present invention relates to a biomaterial fabrication process for the manufacture of a collagen based fabric for an aligned collagen fiber network.

14 Claims, 11 Drawing Sheets

11A  Threads and Tubes Composed of Dextran

11B  Circular Fabrics Composed of Hydroxypropyl Cellulose and Dextran

TEMPLATED ASSEMBLY OF COLLAGEN FIBERS AND USES THEREOF

CROSS-REFERENCE TO RELATED APPLICATIONS

This application claims the benefit of and priority under 35 U.S.C. § 371 to International Patent Cooperation Treaty Application No. PCT/CA2018/050097, filed Jan. 26, 2018, which claims the benefit of priority to U.S. Provisional Patent Application No. 62/450,828, filed Jan. 26, 2017, the entire contents of both disclosures are incorporated herein by reference in their entireties.

TECHNICAL FIELD

The present invention relates generally to polymer-templated and aligned collagen fibers and fabrics derived from collagen doped dextran compositions and uses thereof.

BACKGROUND

Collagen is the most abundant protein in the human body. It is a key structural component of a variety of tissues and serves as a substrate for cell attachment and growth. One of the defining features of collagen is its ability to naturally form fibers in the human body. However, collagen fibers have been notoriously difficult to recreate in the laboratory.

Methods for the isolation of collagen fibers for surgical applications such as sutures or in the form of hemostatic fleece or as wound dressing material and other uses have been known. Collagens are widely used as biomaterials in drug-delivery and tissue engineering applications due to their biodegradability, biocompatibility and hypoallergenicity. In the above surgical applications, it is important that the collagenous material, specifically the collagen fibers, retain their native structure. For this reason, the method of isolation and purification of collagen fiber from the starting material should extract all non-collagenous components of the original tissue without denaturing the original crystalline structure of collagen.

Several patents describe the method of isolating microfibrillar collagen as a hemostatic agent or reconstituting surgical structures from solubilized collagen gels. According to the Battista patent (U.S. Pat. No. 3,742,955), fluffy, finely divided microfibrils of collagen are produced. The length of the fibrils, amounting to an average of 100 µm, does not allow further textile processing. Several other patents refer to procedures resulting in complete disintegration of the fibrillar structure of collagen. By their process, a gel of dispersed collagen molecules is reconstituted by a complex process into fibrillar form by an extrusion into a precipitating medium. (Veis et al, U.S. Pat. No. 2,838,363; Smith, U.S. Pat. No. 3,527,225; Grisef et al, U.S. Pat. Nos. 3,114,372 or 3,114,593 or 3,511,904; Nichols et al, U.S. Pat. No. 3,520,402).

Koob et al. have described methods of producing nordihydroguaiaretic acid (NDGA) polymerized collagen fibers for various biomedical applications, some with tensile strengths similar to natural tendon (e.g., about 91 MPa). See, for example, Koob and Hernandez, Material properties of polymerized NDGA-collagen composite fibers: development of biologically based tendon constructs, Biomaterials 2002 January; 23 (1): 203-12; and U.S. Pat. No. 6,565,960, the contents of which are hereby incorporated by reference as if recited in full herein.

More recently, man-made collagen fibers can be manufactured using a wet-spinning technique yielding fiber diameters higher than 8 µm, or by electrospinning techniques. Biocompatible collagen scaffolds have been described in the art, for example, A Nakada et al. ("*Manufacture of a weakly denatured collagen fiber scaffold with excellent biocompatibility and space maintenance ability*", Biomedical Materials, (2013), Vol. 8(4)). The authors made a weakly denatured collagen fiber scaffold from a collagen fiber suspension (physiological pH 7.4) through a process of freeze drying and denaturation with heat under low pressure ($1 \times 10^{-1}$ Pa). Heat treatment formed cross-links between the collagen fibers, providing the scaffold with sufficient mechanical strength to maintain the space for tissue regeneration in vivo. A weakly denatured collagen fiber scaffold with moderate biocompatibility and space maintenance ability was made by freezing at −10° C., followed by denaturation at 140° C. for 6 h. In addition, the direction of the collagen fibers in the scaffold can be adjusted by cooling the suspension only from the bottom of the container. This process increased the ratio of cells that infiltrated into the scaffold.

A weakly denatured collagen fiber scaffold thus made can be used for tissue regeneration or delivery of cells or proteins to a target site. Electrospinning of collagen has attracted considerable attention in recent years, because this process is capable of producing nanofiber structures that resemble native collagen fibrils, and offers the ability to manipulate the porosity, structure, and orientation of the collagen fiber network. While ordered fiber networks and sufficient porosity for cellular infiltration can be difficult to achieve due to the random nature of electrospun fiber deposition, methods have been developed to increase alignment and pore size with the addition of sacrificial fibers. However, these processes require highly specialized electrospinning equipment. In addition, harsh solvents, such as fluoroalcohols, are often used to stabilize jets of dissolved collagen during the electrospinning process. Unique characteristics of these solvents allow them to optimally evaporate from self-assembling collagen fibers and minimize wet fiber deposition. However, solvent exposure can denature collagen and increase its solubility upon subsequent contact with aqueous environments.

The electrospinning process also exposes collagen to high shear forces, which can limit its ability to self-assemble into a stable conformation. Electrospun collagen fibers must therefore be crosslinked prior to use as a biomaterial to avoid collagen dissolution in aqueous environments, which is not ideal because residual crosslinking agents may interfere with downstream applications. Extrusion-based collagen fibrogenesis can also produce self-assembled collagen fibers and does not require electrostatic forces or solvents. However, this process is slow and only produces one relatively thick fiber at a time. Attempts have been made to streamline this technique and generate aligned collagen networks, but once again the use of specialized equipment and the thickness of the fibers that are formed limit this method. Finally, there have been several examples of collagen fiber assembly in microfluidic devices that while effective at promoting organization and alignment of collagen fibers of appropriate sizes, have severe limitations in throughput and format that limit downstream applications.

There remains a need to develop methods for production of templated collagen fibers that exclude the use of toxic chemicals and laborious processes that generate aligned templated biocompatible collagen fibers suitable for forming two-dimensional and three-dimensional collagen constructs that can be used in bioengineering and wound healing medical applications.

There is also a need to develop collagen fibers that are shelf-stable for long periods of time at temperatures encountered during storage, shipping and end use (e.g., between −20° C. and 40° C.). This eliminates the need for the collagen products to be transported and maintained using the cold chain. Alternatively, collagen materials can be subjected to freeze-drying procedures to extend their shelf life, but these procedures are known to affect the final structure of the biomaterial product. Thus, production of collagen fibers that can be rapidly dried as they are produced without the need for freezing under vacuum is highly-desirable from a manufacturing perspective.

Further, such a material would not require intensive sterilization procedures used to prepare biomaterial products derived from human or animal tissues (e.g., decellurized matrices or grafts) and would decrease reliance on antimicrobial storage buffers or other specialized aqueous storage solutions that are sometimes used to prevent microbial growth on biomaterials and prolong shelf life for materials that must be stored under hydrated conditions.

SUMMARY

It is to be understood that the present invention includes a variety of different versions or embodiments, and this Summary is not meant to be limiting or all-inclusive. This Summary provides some general descriptions of some of the embodiments, but may also include some more specific descriptions of other embodiments.

The present invention relates to a biomaterial fabrication process that uses long-chain polymers such as dextran for the manufacture of a collagen-based fabric for an aligned collagen fiber network, the process comprising: a. providing a collagen-dextran polymer (CDP) composition comprising dextran and collagen; b. applying the CDP composition to a first surface of a first substrate; c. contacting the CDP composition with a first surface of a second substrate, thereby interposing the substrate solution between the first substrate and the second substrate; d. forming a plurality of elongated CDP composition fibers by pressing and separating the first and second substrates along a horizontal axis thereby elongating the substrate solution and forming the plurality of elongated CDP composition fibers; e. placing the collected elongated CDP fibers onto a positionable stage thereby forming a precursor layer of collected CDP composition fibers; and f. contacting the precursor layer with a solvent to dissolve the dextran in the collected CDP composition fibers thereby forming the collagen based fabric.

In a second aspect, the present invention provides a method for producing a 2-D or a 3-D collagen fiber network construct, the method comprising: a. providing a collagen-dextran polymer (CDP) fabric comprising CDP fibers; and b. contacting the CDP fabric on at least one surface of a porous hydrogel matrix.

Many of the problems associated with shelf-life of existing collagen fibers using manufacturing methods to date are overcome by the methods and compositions of the present disclosure. It is likely that the disclosed dried fibers illustrated herein would be compatable with other forms of sterilization that may be easier to perform, e.g., ethylene oxide gas, gamma irradiation or even autoclave.

BRIEF DESCRIPTION OF THE DRAWINGS

FIG. 1A depicts synthesis of the CDP fibers.

FIG. 1B depicts a schematic representation of the positionable stage with CDP fibers placed on top.

FIG. 1C depicts a schematic representation of the positionable stage with CDP fibers placed on top in the first cycle, while a second cycle of CDP fiber placement occurs at 90 degrees to the first cycle when the positionable stage is rotated in a clockwise fashion.

FIG. 1D depicts a schematic representation of the positionable stage with CDP fibers placed on top in the first cycle, a second cycle of CDP fiber placement occurs at 90 degrees to the first cycle, and a third cycle of CDP fiber placement on the positionable stage after rotation of the positionable stage 45 degrees clockwise of the first cycle.

Figures 1A, 1B, 1C, 1D:
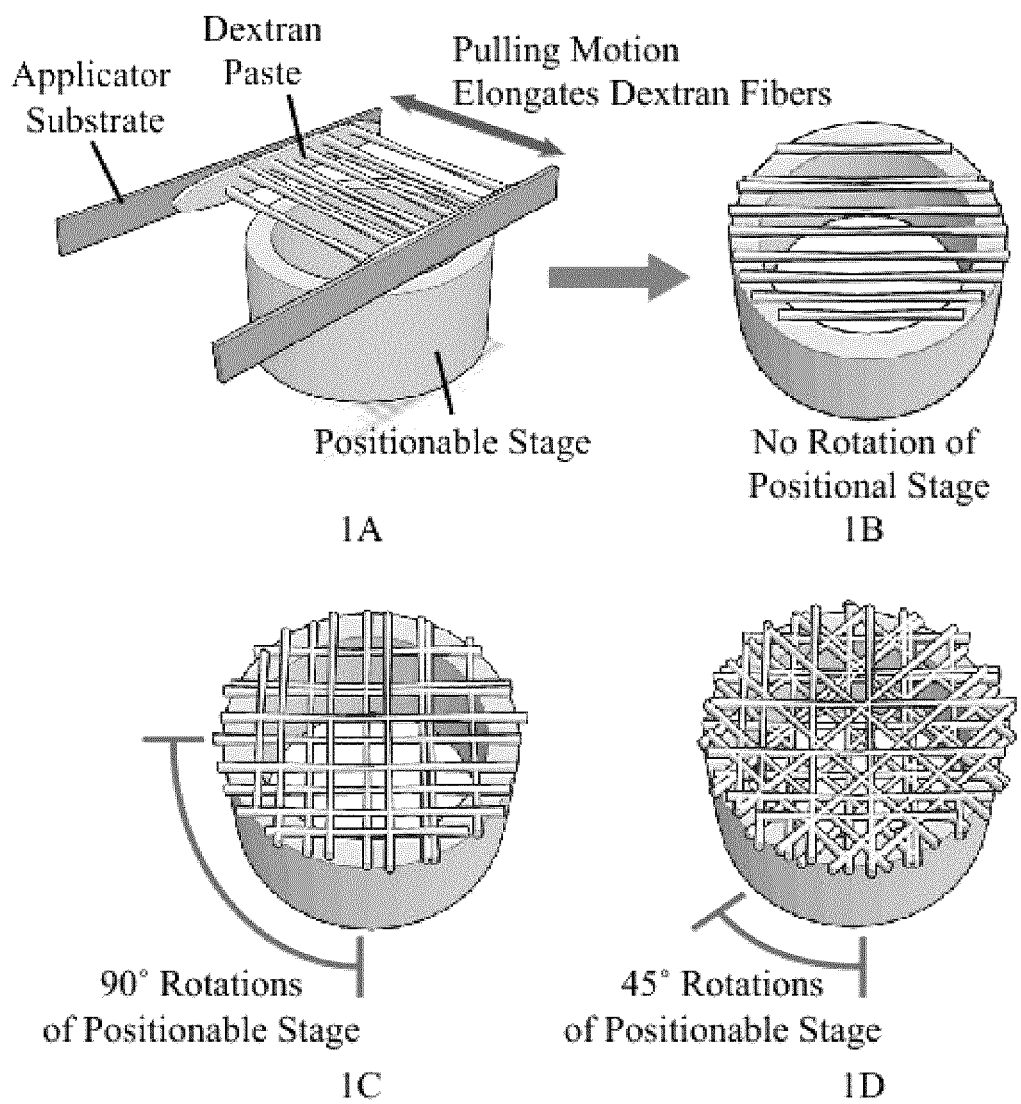
FIGS. 1A-1D depicts a schematic representation of the synthesis of collagen-dextran polymer (CDP) fibers in accordance with several embodiments of the present invention.

These figures are provided by way of example and are not intended to limit the scope of the invention.

DETAILED DESCRIPTION

Definitions

For purposes of this disclosure, unless defined otherwise, technical and scientific terms used herein have the same meaning as commonly understood by one of ordinary skill in the art to which this invention belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Spring Harbor Press (Cold Spring Harbor, N.Y. 1989). These references are hereby incorporated into this disclosure by reference in their entireties.

Before the present compositions and methods are described, it is to be understood that any invention is not limited to the particular processes, compositions, or methodologies described, as these may vary. Moreover, the processes, compositions, and methodologies described in particular embodiments are interchangeable. Therefore, for example, a composition, dosage regimen, route of administration, and so on described in a particular embodiment may be used in any of the methods described in other particular embodiments. It is also to be understood that the terminology used in the description is for the purpose of describing the particular versions or embodiments only, and is not intended to limit the scope of the present invention, which will be limited only by the appended claims. Unless clearly defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

It must be noted that, as used herein, and in the appended claims, the singular forms "a", "an", and "the" include plural reference unless the context clearly dictates otherwise.

Embodiments including the transition phrase "consisting of" or "consisting essentially of" include only the recited components and inactive ingredients.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the description includes both instances where the event occurs and instances where it does not.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

Unless defined otherwise, all technical and scientific terms used herein have the same meaning as commonly understood by one of ordinary skill in the art. Practitioners are particularly directed to Current Protocols in Molecular Biology (Ansubel) for definitions and terms of the art. Abbreviations for amino acid residues are the standard 3-letter and/or 1-letter codes used in the art to refer to one of the 20 common L-amino acids.

The term "amino acid" not only encompasses the 20 common amino acids in naturally synthesized proteins, but also includes any modified, unusual, or synthetic amino acid. One of ordinary skill in the art would be familiar with modified, unusual, or synthetic amino acids.

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied. The terms "peptide(s)", "protein(s)" and "polypeptide(s)" are used interchangeably herein.

As used herein, the term "polypeptide" refers to a polymer of amino acids and does not refer to a specific length of the product. Thus, peptides, oligopeptides, and proteins are included within the definition of polypeptide. This term also does not exclude post-expression modifications of the polypeptide, for example, glycosylations, acetylations, phosphorylations and the like. Included within the definition are, for example, polypeptides containing one or more analogs of an amino acid (including, for example, unnatural amino acids), polypeptides with substituted linkages, as well as other modifications known in the art, both naturally occurring and non-naturally occurring. As is known in the art, "proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. Typically, the amino acids making up a protein are numbered in order, starting at the amino terminal residue and increasing in the direction toward the carboxy terminal residue of the protein.

A polymer may include a compound formed by the covalent joining of smaller molecules, which are referred to herein as residues, or polymer subunits, when incorporated into a polymer. Prior to incorporation into a polymer, the residues typically are described as monomers. Polymers can may have any topology, including, without limitation, straight-chain, branched-chain, star, dendritic, comb, etc. A non-limiting list of useful polymers in the methods and structures described herein includes: dextran and collagen.

The term "isolated" or "purified" polypeptide as used herein refers to a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the proteins and naturally occurring molecules with which it is naturally associated.

As used herein, the term "dextran" means a long chain polysaccharide formed from alpha-1-6 glycosidic linkages of glucose molecules.

As used herein, the term "viscosity" refers to the resistance of a fluid to shear or tensile stress (the "thickness" of a fluid).

As used herein, the term "collagen" generally relates to an abundant helical protein found in connective tissues. Type I, II, III, V, XI are fibrillar collagens that form hierarchical structure ranging from the tropocollagen triple helix to fibers and bundles of fibers are contemplated for use in the present invention.

As used herein, the term "fiber" generally relates to a continuous flexible cylindrical material that is much greater in length than it is cross-sectional diameter. Other expressions for the dimensions of fibers can include As used herein, the term "fabric" refers to a material formed from weaving or aggregating large number of fibers.

As used herein, the term "pre-material" generally relates to a starting mixture or unprocessed material that is manipulated to form a final material, in this case, a viscous solution of dextran and collagen that is elongated and dried into fiber.

A. ISOLATED COLLAGEN TEMPLATED FIBERS

In various embodiments of the present invention, the inventors have discovered a method to produce templated collagen fibers from polymer compositions, for example, compositions containing dextran and collagen (collagen-dextran polymer compositions (CDP)). The produced fibers that can be formed from any of the materials listed in TABLE 1 have controlled lengths and diameters. TABLE 1. Lists polymers capable of forming fibers. These polymers can be utilized to produce alternative polymer formulations useful for templating network of collagen and other materials. Some of these polymers can be cross-linked following fiber formation to produce fibers that do not dissolve when in contact with aqueous solvents.

TABLE 1

Exemplary polymers capable of forming fibers in accordance with the methods described herein.

| Polymer | Supplier | Average Molecular Weight (kDa) |
| --- | --- | --- |
| Dextran | Dextran Products Ltd. | 500 |
| Dextran | Pharmacosmos | 500 |
| Hydroxypropyl Cellulose | Sigma Aldrich | 80 |
| Poly(2-ethyl-2-oxazoline) | Sigma Aldrich | 500 |
| Poly(4-styrenesulfonic acid-co-maleic acid) | Sigma Aldrich | 20 |
| Poly(acrylic acid) | Sigma Aldrich | 450 |
| Poly(diallyldimethyl ammonium chloride) | Sigma Aldrich | 400-500 |
| Poly(methacrylic acid) | Sigma Aldrich | 9.5 |
| Poly(methyl vinyl ether-alt-maleic acid) | Sigma Aldrich | 216 |
| Poly(vinyl alcohol) | Sigma Aldrich | 31 |
| Poly(vinylpyrrolidone) | Sigma Aldrich | 360 |

The collected fibers are then manipulated by laying individual fibers that dry as they are formed onto a positionable substrate. In the case of CDP fabrics, the fabrics are subsequently treated to remove the dextran leaving templated, aligned collagen fibers.

The polymer fibers can be layered on a positionable substrate to form organized fabrics with controlled fiber alignment, overcoming many of the limitations of other fiber-based approaches. Depending on the number of fiber layers and orientation within the fabric, unique mechanical properties can be achieved. In some embodiments, fabrics formed from polymer fibers are also capable of releasing bioactive agents as the fabrics degrade.

In some embodiments, the present invention provides a biomaterial fabrication approach to develop a simple, rapid, and versatile method for generating collagen fibers of appropriate sizes that can be organized into networks to support the two-dimensional (2-D) and three-dimensional (3-D) growth of living cells, for example, skeletal muscle cells, cardiomyocyte cells, neurons, and epithelial cells. The present invention provides a manufacturing process operable to produce an accessible and tunable collagen-based material that may hold promise as a matrix or scaffold for supporting the growth of a wide-variety of additional cell types, and as a material for tissue engineering, wound healing and reconstruction.

B. POLYMER SOLUTIONS

In various embodiments, the CDP compositions used in the methods described herein to make the template and aligned collagen fibers comprise, consist essentially of, or consist of collagen and dextran (collagen-dextran polymer (CDP) compositions). The combination of these biocompatible polymers can be made to tune the diameter, length and rheology of the combined CDP compositions. By "biocompatible," it is meant that a CDP composition and its normal in vivo degradation products are cytocompatible and are substantially non-toxic and non-carcinogenic in a patient within useful, practical and/or acceptable tolerances. By "cytocompatible," it is meant that the CDP compositions are substantially non-toxic to cells and typically and most desirably can sustain a population of cells and/or the polymer compositions, scaffolds, devices, copolymers, and degradation products thereof are not cytotoxic and/or carcinogenic within useful, practical and/or acceptable tolerances. For example, a copolymer composition when placed in a human epithelial cell culture does not adversely affect the viability, growth, adhesion, and number of cells. In one non-limiting example, the co-polymers, compositions, and/or devices are "biocompatible" to the extent they are acceptable for use in a human and a veterinary patient according to applicable regulatory standards in a given legal jurisdiction. In another example the biocompatible collagen, when implanted in a patient, does not cause a substantial adverse reaction or substantial harm to cells and tissues in the body, for instance, the CDP composition or device does not cause necrosis or an infection resulting in harm to tissues organs or the organism from the implanted compositions.

In some embodiments, the CDP compositions comprise, consist essentially of, or consist of collagen:dextran (wt/wt) in ratios ranging from about 1:1000 to about 1:62, more preferably, from about 1:500 to about 1:125 and all integers therebetween. In some embodiments, the ratio of collagen to dextran powder by mass (wt/wt) may range from about 1 part collagen to about 500 parts of dextran to about 1 part collagen to about 125 parts of dextran. In some embodiments, the collagen may be collagen type I, type II, type III, type V, type XI, or combinations thereof. In some embodiments, the source of the collagen may be sourced from a mammalian animal, for example, porcine, bovine, murine, equine, ovine, caprine, human, or combinations thereof. Other sources of collagen type I, type II, type III, type V, type XI, or combinations thereof not specifically recited but which function like those enumerated are contemplated herein, including recombinant collagens and associated reagents. In some embodiments, the collagen used in the preparation of the CDP compositions can include type I collagen from an animal selected from porcine, bovine, murine, equine, ovine, caprine, human, or combinations thereof. For preparation of the CDP compositions, collagen can be used at concentrations ranging from about 0.1 mg/mL to about 100 mg/mL, preferably from about 1 mg/mL to about 50 mg/mL or more preferably from about 1 mg/mL to about 20 mg/mL.

Dextran useful in the CDP compositions described herein may be sourced from a variety of production schemes. Any dextran polymer can find utility in the present invention, for example, a dextran having a long chain polysaccharide formed from alpha-1-6 glycosidic linkages of glucose molecules. In some embodiments, dextran can include Class 1 dextrans containing the $\alpha(1\rightarrow6)$-linked D-glucopyranosyl backbone modified with small side chains of D-glucose branches with $\alpha(1\rightarrow2)$, $\alpha(1\rightarrow3)$, and $\alpha(1\rightarrow4)$-linkage may be used. The class 1 dextrans vary in their molecular weight, spatial arrangement, type and degree of branching, and length of branch chains, depending on the microbial producing strains and cultivation conditions. Isomaltose and isomaltotriose are oligosaccharides with the class 1 dextran backbone structure. Class 2 dextrans (*alternans*) containing a backbone structure of alternating $\alpha(1\rightarrow3)$ and $\alpha(1\rightarrow6)$-linked D-glucopyranosyl units with $\alpha(1\rightarrow3)$-linked branches may be used. Similarly, Class 3 dextrans (*mutans*) having a backbone structure of consecutive $\alpha(1\rightarrow3)$-linked D-glucopyranosyl units with $\alpha(1\rightarrow6)$-linked branches, may be used in formulating the CDP compositions described herein. In some embodiments, dextrans useful for use in formulating the CDP compositions described herein are produced by bacterial or yeast or fungal species, for example, *Leuconostoc* spp. In various embodiments, dextrans useful in the present invention have an average molecular weight ranging from about 40 to about 1,000 kilodaltons, for example, from about 40 kDa. to about 900 kDa., or from about 40 kDa. to about 800 kDa., or from about 40 kDa. to about 700 kDa., or from about 40 kDa. to about 600 kDa., or from about 40 kDa. to about 500 kDa., or from about 40 kDa. to about 400 kDa., or from about 40 kDa. to about 300 kDa., or from about 40 kDa. to about 250 kDa., or from about 100 kDa. to about 1000 kDa., or from about 200 kDa. to about 1000 kDa., or from about 350 kDa. to about 1000 kDa., or from about 450 kDa. to about 1000 kDa., or from about 550 kDa. to about 1000 kDa., or from about 650 kDa. to about 1000 kDa., or from about 750 kDa. to about 1000 kDa. In some embodiments, the dextran has an weight average molecular weight of about 400 kDa. to about 600 kDa., or from about 450 kDa. to about 550 kDa., or about 500 kDa. In various embodiments, the dextran average molecular weight (Mw) can be calculated using the weight average molecular weight (Mw) which can be calculated using gel chromatography or gel permeation chromatography using dextran standards with sequence molecular weights ranging from 8.8, 40, 71.9, 110, 200, 580 and 2000 kDa for the plot of a calibration curve. In some embodiments, the CDP composition is prepared using type 1 collagen and dextran from *Leuconostoc* spp. having a weight average molecular weight of approximately, 500 kDa.

C. METHODS OF MAKING TEMPLATED COLLAGEN FIBERS

The invention further contemplates methods for producing template and aligned collagen fibers from a collagen-dextran polymer composition. An exemplary collagen-dextran polymer (CDP) composition can be made by mixing about 1 part of collagen to about 1000 parts dextran, or more preferably, mixing about 1 part of collagen to about 500 parts dextran, or more preferably, mixing about 1 part of collagen to about 125 parts dextran, or more preferably, mixing about 1 part of collagen to about 62 parts dextran. In various embodiments, the ratio based on (wt/wt%) of collagen to dextran in the CDP composition can range from about 0.1% to about 1.57% collagen to about 99.9% to about 98.43% dextran, or more preferably, the ratio based on (wt/wt%) of collagen to dextran in the CDP composition can range from about 0.2% to about 0.79% collagen to about 99.8% to about 99.21% dextran In certain embodiments, the CDP composition is mixed extensively to produce a viscous paste having a viscosity ranging from about 15,000 centipoise to about 100,000 centipoise, preferably from about 19,000 centipoise to about 90,000 centipoise using the vertical falling ball method and a vertical falling ball viscometer when a solution of the CDP composition is measured at 22°. A falling ball viscometer has a sphere ball that falls down along a tube containing the sample liquid to be measured, and this tube is surrounded concentrically by a tubular jacket for thermal control. The previous theory used Newton's law of motion for describing the falling ball reaching a terminal velocity; thus, the net force of gravity, buoyancy, and drag is zero:

$$W - F_D - F_B - \left(\frac{\pi d^3}{6}\right)\gamma_s - \left(\frac{\pi d^3}{6}\right)\gamma_f - 3\pi\mu u_t d = 0 \quad (1)$$

The drag force is expressed in the third term on the right side of the equal sign according to Stokes' law, which is valid in Ref 1. Eq. (1) can be easily expressed in the following form:

$$\mu = \frac{(\gamma_s - \gamma_f)d^2}{18u_t} \quad (2)$$

Where $\gamma$ is the specific weight, d is the diameter of the sphere, and $u_t$ is the terminal velocity. The subscripts s and f represent the sphere and fluid, respectively. Eq. (2) can be simplified to the following form and is the same as that claimed in the standard:

$$\mu = K \cdot (\rho_s - \rho_f) \cdot t, \text{ where } K = \frac{g \cdot d^2}{18l} \quad (3)$$

Where l is the falling length and t is the time passing the length of l.

When the material properties, geometric properties, and falling time are known, the viscosity can be obtained from Eq. (2) or (3). In the standards, the coefficient of K must be estimated by measuring a reference liquid with a known viscosity. Then, the viscosity of an unknown liquid can easily be calculated in Eq. (3), when the falling time is known.

In certain embodiments, the CDP composition comprises a collagen:dextran mass fraction ranging from about 0.0044 to about 0.008. Once the CDP composition has been produced, the composition can be used to synthesize collagen doped dextran fibers for the manufacture of collagen based fabrics. In some embodiments, the minimum dextran solution viscosity necessary to efficiently form CDP fibers is 19,500 centipoise, as measured by the falling ball method (see above). Various samples of dextran may vary in polymer polydispersity and require modification of concentration to achieve the working viscosity. In addition, if a dextran of different molecular weight is utilized, it may be necessary to optimize the concentration required to produce the desired viscosity, which can be achieved using common techniques known to those of skill in the art. The CDP composition should always fully dissolve in aqueous solutions, although without vigorous mixing it may take up to 24 hours for the dextran to fully dissolve. Solubility of the dextran and/or collagen in the CDP composition may be aided by rapidly and thoroughly mixing the collagen solution and dextran using a pipette tip to obtain a viscous paste in less than 2 minutes of mixing.

In some embodiments, the biofabrication method for the manufacture of a collagen based fabric for an aligned collagen fiber network comprises the steps:
 a. providing a collagen-dextran polymer (CDP) composition comprising dextran and collagen;
 b. applying the CDP composition to a first surface of a first substrate;
 c. contacting the CDP composition with a first surface of a second substrate, thereby interposing the CDP composition between the first substrate and the second substrate;
 d. forming a plurality of elongated CDP fibers by pressing and separating the first and second substrates along a horizontal axis thereby elongating the CDP composition and forming the plurality of elongated CDP fibers;
 e. placing the elongated CDP fibers onto a positionable stage thereby forming a CDP fiber layer or CDP fabric of collected CDP fibers; and
 f. contacting the CDP fiber layer or CDP fabric with a solvent to dissolve the dextran in the CDP fiber layer or CDP fabric thereby forming the collagen based fabric.

In some embodiments, the present invention provides a biofabrication method for the manufacture of a collagen based fabric for an aligned collagen fiber network. In exemplary embodiments, the process comprises the steps: a. providing a collagen-dextran polymer (CDP) composition comprising dextran and collagen; b. extruding the CDP composition through an orifice forming an elongated CDP fiber; c. placing one or more elongated CDP fibers onto a positionable stage thereby forming a CDP fiber layer or CDP fabric; and d. contacting the CDP fiber layer or CDP fabric with a solvent to dissolve the dextran in the CDP fiber layer or CDP fabric thereby forming the collagen based fabric.

In some embodiments, the CDP composition may be spread onto a surface of a first substrate. The first substrate can be any surface that will adhere to the CDP composition. In some embodiments, the first substrate is a planar substrate. The first substrate can be any shape, having at least one surface that may adhere to the CDP composition. The substrate can be made of any solid material, including for example, a metal, a glass, a natural material, for example, carbon, wood, silica and the like. In some embodiments, the CDP composition is applied to the first substrate surface such that it is at least partially spread over the surface of the first substrate. In some embodiments, the CDP composition forms a layer over at least a partial surface area of a surface of the first substrate. In some embodiments, the CDP composition layer may be 10-500 microns thick. Subsequently, a first surface of a second substrate is contacted with the CDP composition layer on the surface of the first substrate to form a CDP composition sandwich between the two substrates. In some embodiments, the second substrate can be any surface that will adhere to the CDP composition. In some embodiments, the second substrate is a planar substrate. The first substrate can be any shape, having at least one surface that may adhere to the CDP composition. The second substrate can be made of any solid material, including for example, a metal, a glass, a natural material, for example, carbon, wood, silica and the like.

To create the CDP fibers, the two substrates are then separated and brought closer together for 2 or more cycles. As the substrates are spread apart, the CDP composition between the two substrates elongates and forms one or more CDP fibers. The elongated CDP fibers are then placed on the surface of a positionable stage. In other exemplary embodiments, the substrates can be tongue depressors, paddles, pipette tips, glass slides. In each of these exemplary embodiments, the substrate surfaces may comprise or be made of a solid material, for example, plastic, wood, glass, silicon, In other embodiments, the CDP composition is made into fibers using any method known in the art to force fluid through an orifice, sufficient to form fibers, for example, the CDP composition can be passed through a receptacle, for example a syringe containing a narrow nozzle (any objects that have orifices that are able to extrude material). In various embodiments, CDP fibers of the present invention are extruded. In some embodiments, extruding a CDP composition can include a syringe pump, a syringe, leader tubing, and a blunt needle through which the CDP composition is extruded to form elongated CDP fibers that are placed on the surface of a positionable stage. In one embodiment, a CDP solution of collagen and dextran is degassed, loaded into the syringe, and connected to the leader tubing and needle. The syringe is placed in position relative to syringe pump so that the pump can act on the syringe to extrude the CDP solution. The leader tubing and needle are placed adjacent to or on top of the positionable stage. Although a syringe pump and syringe are used to illustrate the extrusion of the CDP solution in accordance with the present invention, those of ordinary skill in the art of polymer extrusion will recognize that extrusion can also be carried out by use of other conventional devices.

As used herein a "positionable stage" is a stage, substrate, surface, platform, etc. which can be manipulated in terms of its rotation or positioning in space. The positionable stage can be any material capable of maintaining the length of elongated CDP fibers. The shape of the positionable stage can be square, rectangular, triangular, or circular. It preferably has a first fiber contact region and a second fiber contact region, such that the CDP fiber being generally cylindrical in shape has a first terminal end and a second terminal end. The positionable stage has a portion that is operable to contact the first terminal end of the fiber and a second portion that can contact the second terminal end of the fiber such that the terminal ends of the fiber are supported by the first and second portions of the positionable stage. The positionable stage can be fully planar or hollow in the middle leaving a perimeter that can serve to support the two termini of the CDP fibers. In one exemplary embodiment, the positionable stage can be a body having a substantially cylindrical shape, wherein the body defines an outer surface and an inner surface, a proximal end surface, and a distal end surface wherein each of the proximal end surface and the distal end surface joins the outer surface to the inner surface, and wherein the inner surface defines a passage extending through the body form the proximal end surface to the distal end surface. The passage is accessible from a proximal opening formed by the proximal end surface and a distal opening formed by the distal end surface wherein the passage is defined in an example, by an inner diameter wherein the outer surface is defined by an outer diameter, wherein the body is defined by a thickness extending between the inner surface and the outer surface wherein the body is further defined by a length extending between the proximal end surface and the distal end surface.

In some embodiments, the stage(s) are translational and/or rotational stages that are positionable in that they can be moved in one, two or three dimensions, permitting and facilitating relative motion of, for example, the elongated CDP fibers that are placed on its surface. Movement of the stages in one, two or three dimensions may be accomplished manually or by use of mechanical or electromechanical controllers. The motion of the positional stage(s) can be computer-controlled, such that tasks such as placement of the elongated CDP fibers onto the positional stage can be precisely controlled and repeated—thereby facilitating manufacture of CDP fabrics using the technologies described herein. Design of appropriate and effective mechanical, electrical, computer and robotic systems for performing the steps described herein are well within the abilities of those of ordinary skill in the art of mechanical, electrical, computer and robotic systems design.

In the context of translational movement of a positionable stage, the direction of the movement may be said to have a vector in any direction, meaning it can move in any direction that exhibits movement along the stated axis. Rotating a spinning form of the positional stage in relation to the elongated CDP fibers will have an effect on the deposition pattern of said fibers.

In various embodiments, 5 or more elongated CDP fibers are collected and placed on the surface of the positional stage per cycle, with multiple cycles of CDP fiber placement resulting in controlled, templated fiber fabrics. Rotating the positional stage in either clockwise or counter clockwise fashion will create for example, orthogonal or other directional orientation of the CDP fibers thereby making a CDP fabric that can have controlled placement of the fibers and controlled spacing between the fibers.

Once the elongated CDP fibers have been placed on the positional stage in one or more placement cycles, the CDP fabric can be left to dry under ambient conditions, or they may be dried by placing the fabric in a temperature and/or humidity controlled environment. The next step in the preparation of the collagen-based fabric requires the removal of the dextran from the CDP fabric. In some embodiments, the CDP fibers or CDP fabric may be hydrated to dissolve the dextran leaving a layer of fibers, or a plurality of layers of fibers (a fabric) comprised entirely of collagen. Hydration may be performed in an aqueous solution. For example, illustrative aqueous solutions can include, but not limited to: water, a phosphate buffer, 0.9% NaCl physiological saline, 50 mM Tris, 150 mM NaCl Tris-buffered saline, lactated Ringer's solution, Ringer-acetate solution, tissue culture media, or combinations thereof. The resulting collagen fibers are not stable in water. Hydration can be carried out by dropping the collagen fibers or collagen fabric directly into the liquid. In some embodiments, to prevent the collagen fibers from breaking or losing their orientation because of air-liquid interfacial forces and convection from rapid dextran dissolution, the fibers or fabric can be gently hydrated on a semi-wet substrate such as a hydrogel.

The dry collagen fabric morphology (fiber diameter, length, orientation, density (fibers/mm$^2$)) may be characterized by darkfield stereomicroscopy. It is also possible to characterize the collagen fiber morphology by scanning electron microscopy. In addition, dry fabric tensile properties can be measured. If the collagen fibers or collagen fabric is hydrated, the hydrated collagen fibers may be characterized by phase-contrast microscopy, polarized light microscopy to observe birefringence, immunofluorescent staining with antibodies targeted to the non-denatured helical form of collagen, aniline blue staining, or by observing aligned cell attachment and growth. In various embodiments, the resultant hydrated collagen fibers thus produced in accordance with the present methods described herein, may have diameters ranging from about 0.1 μm to about 500 μm, or from about 1 μm to about 100 μm. In various embodiments, the collagen fibers thus produced in accordance with the several embodiments of the present invention, have lengths ranging from 1 mm to 10 m, for example, 1 mm to about 5 m, or for example, 1 mm to about 10 cm. Accordingly, the collagen fibers produced in accordance with the methods described herein have aspect ratios (diameter of fiber:length of fiber) ranging from about $1:2\times10^3$ to about $1:1\times10^9$.

D. METHODS FOR USING TEMPLATED COLLAGEN FIBERS AND COLLAGEN FABRICS

In some embodiments, the CDP composition may be used to produce a plurality of collagen doped dextran fibers. In some embodiments, the collagen fibers produced in the methods described herein can be used to construct 2-dimensional (2-D) or three-dimensional (3-D) biological scaffolds and methods of preparing biological scaffolds are provided. As used herein, a "biological scaffold" refers to a scaffold to be used with biological materials, such as proteins, cells, organelles, organs, or organisms. Nonlimiting examples of cells include, but are not limited to, progenitor cells isolated from the peripheral blood, or bone that can be induced to differentiate into different cells, stem cells, committed stem cells, and/or differentiated cells may be used. Also, depending on the type of tissue or organ being made, specific types of committed stem cells can be used. For instance, myoblast cells can be used to build various muscle structures. Other types of committed stem cells can be used to make organs or organ-like tissue such as heart, kidney, liver, pancreas, spleen, bladder, ureter and urethra. Other cells include, but are not limited to, endothelial cells, muscle cells, smooth muscle cells, fibroblasts, osteoblasts, myoblasts, neuroblasts, fibroblasts, glioblasts; germ cells, hepatocytes, chondrocytes, keratinocytes, cardiac muscle cells, connective tissue cells, epithelial cells, hormone-secreting cells, cells of the immune system, neurons, cells from the heart, kidney, liver, pancreas, spleen, bladder, ureter and urethra, and the like. In some embodiments, it is unnecessary to pre-select the type of stem cell that is to be used, because many types of stem cells can be induced to differentiate in an organ specific pattern once delivered to a given organ. For example, a stem cell delivered to the liver can be induced to become a liver cell simply by placing the stem cell within the biochemical environment of the liver.

Examples also include cells that have been genetically engineered, transformed cells, and immortalized cells. One example of genetically engineered cells useful in the present invention is a genetically engineered cell that makes and secretes one or more desired molecules. When 2-D or 3-D collagen fiber network constructs comprising genetically engineered cells are implanted in an organism, the molecules produced can produce a local effect or a systemic effect, and can include the molecules identified above as possible substances.

Cells may produce substances that inhibit or stimulate inflammation; facilitate healing; resist immunorejection; provide hormone replacement; replace neurotransmitters; inhibit or destroy cancer cells; promote cell growth; inhibit or stimulate formation of blood vessels; augment tissue; and to supplement or replace the following tissue, neurons, skin, synovial fluid, tendons, cartilage, ligaments, bone, muscle, organs, dura, blood vessels, bone marrow, and extracellular matrix. Biological 2-D or 3-D collagen fiber network constructs of the present invention are typically biocompatible and may be bioerodible. Bioerodible scaffolds dissolve over a fixed time period when placed in vivo and/or in culture in vitro.

In some embodiments, collagen fabrics produced in accordance with the present invention find use in the manufacture of 2-D or 3-D collagen fiber network constructs. In some embodiments, methods for making a 2-D or 3-D collagen fiber network construct can include the steps: providing a collagen based fabric comprising elongated CDP fibers; and placing at least one surface of the collagen based fabric on the surface of a porous hydrogel matrix. 2-D and 3-D collagen fiber network constructs can be made by placing either the CDP fibers or CDP fabric within or on the surface of a porous hydrogel material. Optionally, the dextran can be removed from the CDP fibers or CDP fabric and immersing or placing the resultant collagen fibers or collagen fabric into the porous hydrogel material or on the surface of the porous hydrogel material. In some embodiments, the CDP fibers or CDP fabric, or collagen fibers or collagen fabric of the present invention can be treated with cellular growth factors, cytokines, differentiation factors, antibodies, nucleic acids lipids and other factors or biological agents that may attract, help grow, differentiate, or affect some biological function of cells that are contacted with the 2-D or 3-D collagen fiber network construct. CDP fibers or CDP fabric, or collagen fibers or collagen fabric of the present invention can be treated with additives or drugs prior to implantation (before or after the CDP fibers or CDP fabric, or collagen fibers or collagen fabric is seeded with cells), e.g., to promote the formation of new tissue after implantation. Thus, for example, growth factors, cytokines, extracellular matrix components, and other bioactive materials can be added to the CDP fibers or CDP fabric, or collagen fibers or collagen fabric to promote graft healing and formation of new tissue. Such additives will in general be selected according to the tissue or organ being reconstructed or augmented, to ensure that appropriate new tissue is formed in the engrafted organ or tissue (for examples of such additives for use in promoting bone healing, see, e.g., Kirker-Head, C. A. Vet. Surg. 24 (5): 408-19 (1995)). For example, vascular endothelial growth factor (VEGF, see, e.g., U.S. Pat. No. 5,654,273 herein incorporated by reference) can be employed to promote the formation of new vascular tissue. Growth factors and other additives (e.g., epidermal growth factor (EGF), heparin-binding epidermal-like growth factor (HBGF), fibroblast growth factor (FGF), cytokines, genes, proteins, and the like) can be added in amounts in excess of any amount of such growth factors (if any) which may be produced by the cells seeded on the substrate. Such additives are preferably provided in an amount sufficient to promote the formation of new tissue of a type appropriate to the tissue or organ, which is to be repaired or augmented (e.g., by causing or accelerating infiltration of host cells into the graft). Other useful additives include antibacterial agents such as antibiotics.

In one non-limiting embodiment, CDP fibers or CDP fabric, or collagen fibers or collagen fabric of the present invention can be further treated to provide a biocompatible surface. For example and without limitation, the CDP fibers or CDP fabric, or collagen fibers or collagen fabric of the present invention can be treated to provide a sterilized surface for proteins and/or cells. Non-limiting examples of sterilization treatments include: exposure to ultraviolet light; irradiation, such as gamma irradiation; exposure to aseptic solvents, such as ethanol; and exposure to plasma. In another non-limiting example, the CDP fibers or CDP fabric, or collagen fibers or collagen fabric of the present invention can be treated with an agent to provide for a biocompatible and/or cytocompatible surface. Non-limiting examples of agents include: proteins growth factors, antibodies, nucleic acids molecules, carbohydrates, and the like. Growth factors useful in the present invention include, but are not limited to, transforming growth factor-alpha (TGF-α), transforming growth factor-beta (TGF-β), platelet-derived growth factors (PDGF), fibroblast growth factors (FGF), including FGF acidic isoforms 1 and 2, FGF basic form 2 and FGF 4, 8, 9 and 10, nerve growth factors (NGF) including NGF 2.5 s, NGF 7.0 s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, beta3, skeletal growth factor, bone matrix derived growth factors, and bone derived growth factors and mixtures thereof.

Cytokines useful in the present invention include, but are not limited to, cardiotrophin, stromal cell derived factor, macrophage derived chemokine (MDC), melanoma growth stimulatory activity (MGSA), macrophage inflammatory proteins 1 alpha (MIP-1alpha), 2, 3 alpha, 3 beta, 4 and 5, IL-1, IL-2, IL-3, IL-4, IL-5, IL-6, IL-7, IL-8, IL-9, IL-10, IL-11, IL-12, IL-13, TNF-α, and TNF-β. Immunoglobulins useful in the present invention include, but are not limited to, IgG, IgA, IgM, IgD, IgE, and mixtures thereof. Some preferred growth factors include VEGF (vascular endothelial growth factor), NGFs (nerve growth factors), PDGF-AA, PDGF-BB, PDGF-AB, FGFb, FGFa, and BGF.

Other molecules useful as therapeutic or biological agents include, but are not limited to, growth hormones, leptin, leukemia inhibitory factor (LIF), endostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, and interferon 1 alpha.

Embodiments involving amino acids, peptides, polypeptides, and proteins may include any type or combinations of such molecules of any size and complexity. Examples include, but are not limited to structural proteins, enzymes, and peptide hormones. These compounds can serve a variety of functions. In some embodiments, the CDP fibers or CDP fabric, or collagen fibers or collagen fabric may be contacted with peptides containing a sequence that suppresses enzyme activity through competition for the active site. In other applications, antigenic agents that promote an immune response and invoke immunity can be incorporated into a construct. In substances such as nucleic acids, any nucleic acid can be present. Examples include, but are not limited to deoxyribonucleic acid (DNA), and ribonucleic acid (RNA). Embodiments involving DNA include, but are not limited to, cDNA sequences, natural DNA sequences from any source, and sense or anti-sense oligonucleotides. For example, DNA can be naked (e.g., U.S. Pat. Nos. 5,580,859; 5,910,488) or complexed or encapsulated (e.g., U.S. Pat. Nos. 5,908,777; 5,787,567). DNA can be present in vectors of any kind, for example in a viral or plasmid vector. In some embodiments, nucleic acids used will serve to promote or to inhibit the expression of genes in cells inside and/or outside the electrospun matrix. The nucleic acids can be in any form that is effective to enhance its uptake into cells.

In use, the CDP fibers or CDP fabric, or collagen fibers or collagen fabric of the present invention, may be deposited on any suitable cell culture vessel, including plastic or glass vessels, such as flasks, plated, bottles, or any suitable container for culturing cells or tissue, or on the surface of any adherent or non-adherent hydrogel, and then incubated with tissue culture medium and/or low gelling point agarose or polyacrylamide hydrogels to form 2-D or 3-D collagen fiber network constructs.

In some embodiments, the present invention provides a method for producing a 2-D or a 3-D collagen fiber network construct, the method comprising: a. providing a collagen-dextran polymer (CDP) fabric comprising CDP fibers as described above; and b. contacting the CDP fabric on at least one surface of a porous hydrogel matrix.

These 2-D or a 3-D collagen fiber network constructs allow cells to attach, align and grow in patterns that most represent growth and/or differentiation of these cells or cells like them in natural tissue. According to one aspect of the methods described herein, methods of growing cells are provided. As used herein, "growing cells" refers to maintaining cells in culture, including but not limited to adhesion, proliferation, migration, differentiation, and/or aggregation of cells. As described herein, cell migration, orientation and shape can be dictated by the collagen fiber orientation of the 2-D or 3-D collagen fiber network prepared according to the methods described herein. In one non-limiting embodiment, myotubules can be manufactured by depositing a muscle precursor cell onto bundles of substantially parallel fibers of collagen alone or in combination with other polymers. Liver cells can be grown crossed layers of collagen fibers. Neurons from neural stem cells could be harnessed in higher concentrations on such scaffolds. Other cells that can be incorporated into 2-D or 3-D collagen fiber network constructs of the present invention can include, fibroblasts, chondrocytes, osteoblasts, myocytes, hepatocytes, neurons, and cell precursors, such as embryonic stem cells, adipose cells, hair follicle stem cells, cardiac stem cells, myoblasts, neuronal stem cells, and mesenchymal stem cells. In some embodiments, the 2-D and/or 3-D collagen fiber network construct may also contain a bioactive agent, which may include, small molecule drugs, anti-fungal/antimycotics, clotting factors, cytokines, chemokines, therapeutic antibodies, ionic metals, metal salts, organic and inorganic nanoparticles and nanomaterials, nanomaterials assemblies, glass particles, synthetic and natural polymer microparticles, synthetic and natural polymeric matrix materials, laminin, elastin, fibronectin, proteoglycans, other types of collagen, enzymes, gene constructs (siRNA, plasmids, virus, etc.), microbubbles, eukaryotic and prokaryotic cells.

In one embodiment, 2-D or 3-D collagen fiber network constructs prepared according to the methods described herein, can be used to organize muscle cells into fascicle-like structures. In muscle tissue, fascicles are present in various patterns, giving rise to unique force generation properties within the tissue. Within each fascicle, groups of muscle cells are organized by collagen fibers, which can extend along or across muscle cells, before eventually inserting into tendons. The 2-D or 3-D collagen fiber networks prepared according to the present invention are especially well suited for fabricating tissue models that display this pattern of collagen fiber and cell alignment.

An attractive feature of the 2-D or 3-D collagen fiber network as described herein, is that it allows cells encapsulated within hydrogels to elongate and grow into networks. This is one of the most challenging aspects of 3-D cell culture that limits the applicability of many hydrogel systems as in vitro models and as materials for regenerative medicine. In addition to myotube formation in skeletal muscle, various other cell types such as neural cells and vascular cells depend on network formation for appropriate physiological function. Since collagen has been demonstrated to support the growth of these cell types and many other cell types, the invention described herein may prove beneficial to constructing many different types of model tissues. Moreover, since the 2-D or 3-D collagen fiber network produced in accordance with the present invention is a free-standing structure, it is highly versatile and can be applied to functionalize many other types of hydrogel scaffolds and surfaces, e.g., other non-adherent hydrogels such as alginate or polyethylene glycol diacrylate.

Cells can be grown in culture media appropriate for growth and differentiation of any given cell type. Growth factors and cytokines, as are known in the art, can be used to induce cellular growth and differentiation. The choice of cells to propagate within the matrix depends on the intended use. Stem cells (totipotent, pluripotent or multipotent) or other precursor cells would be useful for producing many cell types. Muscle progenitor cells would be useful for producing muscle tissue. Hepatocytes would be useful for producing liver tissue. Aortic cells or cardiomyocytes would be useful for producing aortic or cardiac muscle tissue. Neural stem cells would be useful for producing nerve tissue. Different form shapes can be manufactured for different end uses.

Other exemplary uses, include but are not limited to: 1) Reconstruction and healing of cutaneous and mucous membrane injuries (for example, burns, abrasions, surgical excisions, infections and ulceration); 2) Musculoskeletal system reconstruction (including individual tissue components such as, muscle, tendon and bone as well as combinations of distinct tissue components and interfaces between components). This would be useful for surgical reconstruction following traumatic injury from traumatic injuries such as battlefield injuries, car accidents, severe necrosis from infection or envenomation, and sports injuries as well as many other injuries; and 3) Cardiovascular and nervous system repair: for example, patches for repairing cardiac damage, component materials for bio-artificial heart valves and stents, tubular constructs for nerve or vascular repair/guidance, hemostatic fibers to control bleeding during vascular surgery. Other uses can be readily envisioned by one of ordinary skill in the art to heal damaged tissue, to create tissue engineered materials for replacing or augmenting healthy or damaged tissue, and for many drug delivery systems (medicaments, growth factors, cytokines etc.) requiring non-immunogenic, short term (1 day to 3 months) or long term (>3 months) drug delivery to a subject in need thereof.

E. ARTICLES OF MANUFACTURE

The present invention also provides CDP fibers useful in the manufacture of various articles that incorporate template and aligned collagen fibers. In some exemplary embodiments, articles of manufacture incorporating the collagen fibers of the present invention may be useful in the manufacture of articles for use the field of biotechnology and/or medicine. In some illustrative examples, such articles could include: fabrics for augmenting cell growth in two-dimensional and three-dimensional cell culture conditions. Additional applications include delivery of drugs (for example, hemostatic agents and antibiotics) for use as advanced wound healing materials.

Additionally, the threads/fibers of the present invention can be used to construct engineered tissue organ constructs, or parts of organ constructs e.g., heart, heart valves, liver, kidney, and the like. The ability to use textile-like materials and matrices to bioengineer tissue or organs creates a wide variety of bioengineered tissue replacement applications. Examples of bioengineered components include, but are not limited to, blood vessels, heart, liver, kidney, skeletal muscle, cardiac muscle, and nerve guides. In some embodiments, such matrices are combined with therapeutic agents that improve the function of the implant. For example, antibiotics, anti-inflammatories, local anesthetics or combinations thereof, can be added to the matrix of a bioengineered organ to speed the healing process and reduce discomfort.

G. EXAMPLES

Example 1. Production of CDP Elongated Fibers Containing CDP Compositions

Materials Used

Building block dextran (molecular weight 500,000 g/mol) from Dextran Products Ltd. (Scarborough, ON Canada). Specific rotation (2 wt. % solution) of +195° and intrinsic viscosity (1 wt. % solution, 37° C.) of 0.58 dL/g. High-purity technical quality dextran (molecular weight 500,000 g/mol) from Pharmacosmos (Holbaek, Denmark). Both types of dextran have similar viscosities. The viscosity of dextran solutions was calculated by the falling ball method. A spherical stainless steel ball bearing of 0.399 cm in diameter and 0.2611 g in weight, as measured using a digital caliper accurate to 0.02 mm and an analytical balance accurate to 0.1 mg, respectively, was used to perform the test inside a polystyrene conical tube. A digital timer accurate to 1 msec and a ruler accurate to 0.5 mm were used to record the time and distance traveled by the ball through 35, 40, 45, 50 and 55 wt % dextran dissolved in water. Prior to testing, the dextran solutions were cleared of air bubbles by centrifugation at 3000 rcf for 15 minutes. The density of each dextran solution was then measured using a handheld oscillating u-tube densitometer accurate to 0.001 g/cm3.

Results: Viscosity was computed according to $$\frac{2(\Delta P)ga^2}{9v}$$

where (ΔP) is the difference in density between the dextran solution and the ball bearing, g is the acceleration due to gravity, a is the radius of the ball bearing and v is the velocity of the ball bearing traveling through the dextran solution.

Density of dextran solutions—Density increases linearly as a function of dextran wt %. The calculated regression was y=0.0044x+0.9937. The 55% dextran solution was too viscous to measure using the u-tube densitometer, thus a value of 1.2357 (y=0.0044×55+0.9937) was used for viscosity calculation base on extrapolated data.

Both form fibers. Collagen Type I (Rat Tail, High Concentration) was purchased from Corning (Corning, N.Y. USA). All other chemicals were reagent grade or better and were used without further modification or purification.

Process

1. Blend dry dextran (1 g) with ultrapure water/collagen (1 g) by stirring vigorously with a pipette tip to produce a viscous paste of 50% dextran.

2. Apply a thin layer of 50% dextran paste to two sterile tongue depressor sticks.

3. Repeatedly press together and pull apart the sticks such that fibers of highly-viscous dextran elongated between the two sticks.

4. Collect the dry elongated fibers over the top of a 5.5 cm diameter beaker.

5. Repeat this procedure the desired number of times, while rotating the beaker a predetermined angle between each cycle.

6. Store the dry fabric under ambient conditions until use.

Example 2. 2-D Polyacrylamide Hydrogel Fabrication (2-D Collagen Fiber Network Construct 1. Activate clean glass coverslips (22×22 mm) on a 95° C. hotplate by covering with 500 µL 0.1N NaOH.

2. Evaporate the NaOH and apply 500 µL of ddH$_2$O to improve the uniformity of the surface coating. Then, evaporate the ddH$_2$O.

3. Treat the NaOH-coated coverslips with a 4% solution of (3-Aminopropyl)triethoxysilane in acetone for 15 min at room temperature, wash three times in ddH$_2$O and air-dry.

4. Treat the coverslips with a 0.8% solution of glutaraldehyde in PBS for 1 hour at room temperature, wash three times in ddH$_2$O and air-dry.

5. Form uniform polyacrylamide hydrogels (shear modulus ~8.64) from solutions consisting of 7.5% acrylamide, 0.3% bis-acrylamide, 0.08% ammonium persulfate and 0.001% TEMED between the glutaraldehyde-coated coverslips (binding) and glass slides treated with trichlorosilane (release).

6. Remove the polymerized acrylamide coverslips from the slides and washed three times in ddH$_2$0.

7. To provide sites for attachment of collagen fibers, functionalize the polyacrylamide surfaces by incubation in a 2 mg/mL solution of sulfo-SANPAH under UV light for 5 minutes.

8. Wash the coverslips five times in ddH$_2$0 and a final time in DMEM.

9. Remove the DMEM, apply dry collagen fabrics (~10 layers thick) to the acrylamide surfaces and allow the collagen fibers to attach for 1 hour.

10. Incubate in culture medium and add cell suspensions for attachment to collagen fibers.

Example 3. 3-D Agarose Hydrogel Fabrication (3-D Collagen Fiber Network Construct 1. Dissolving SeaPlaque™ Agarose (Lonza, Rockland, Me. USA) in serum-free culture medium to a concentration of 2 wt. % at temperatures above 70° C.

2. Hold the agarose solution at 37° C. in a water bath during cell preparation.

3. Add an equal volume of warm cell suspension (20×10$^6$ cells/mL) to the 2% agarose to achieve a final cell concentration of 10×10$^6$ cells/mL and a final agarose concentration of 1%.

4. Place 75 µL of this mixture onto a ~15 mg CDP-fabric contained within a 6-well culture plate.

5. After 5 minutes of gelation, add 2 mL of room temperature culture medium.

Example 4. Templated Assembly of Collagen Fibers Directs Cell Growth in 2-D and 3-D A biomaterial fabrication approach to develop a simple, rapid, and versatile method for generating collagen fibers of appropriate sizes that can be organized into networks to support the two-dimensional (2-D) and three-dimensional (3-D) growth of skeletal muscle cells. The manufacturing process produces an accessible and tunable collagen-based material that may be used as a matrix for supporting the growth of a wide-variety of additional cell types, and as a material for wound healing and tissue reconstruction.

Example 5. Methods

Materials and Reagents

Building block dextran (molecular weight 500,000 g/mol) from Dextran Products Ltd. (Scarborough, ON Canada) was used for optimization of the fiber formation process. Based on the manufacturer's certification tests, the specific rotation (2 wt. % solution, $[\alpha]_D^{20}$) was +195° and the intrinsic viscosity (1 wt. % solution, 37° C.) was 0.58 dL/g. Dextran fabrics used in cell culture experiments were formed using high-purity technical quality dextran (molecular weight 500,000 g/mol) from Pharmacosmos (Holbaek, Denmark). Collagen Type I (Rat Tail, High Concentration) was purchased from Corning (Corning, N.Y. USA). All other chemicals were reagent grade or better and were used without further modification or purification.

CDP Fabric Formation

To produce CDP elongated fibers and fabrics, an analytical balance was used to weigh 1 part of dextran powder (e.g. ~1 g) on a plastic weigh boat. Type I collagen was weighed to an appropriate concentration (between 2 mg/mL and 8 mg/mL) in distilled, de-ionized water. A micropipette was used to dispense 1 part collagen solution (e.g. ~1 ml or 1 g of solution) into the weigh boat containing the dextran. Using a pipette tip, the collagen solution and dextran were thoroughly mixed until a viscous paste formed. The pre-material was used within 15 minutes to limit evaporative water loss. A thin layer of the CDP composition paste was then applied to two sterile tongue depressor sticks. The sticks were repeatedly pressed together and pulled apart such that fibers of highly-viscous CDP composition elongated between the two sticks. After each cycle of pressing and pulling, the dry elongated CDP fibers were collected over the top of a 5.5 cm diameter beaker as shown diagrammatically in FIG. 1. Repeated cycles yielded dense, multi-layer fabrics that could be trimmed for removal from the beaker and stored dry at room temperature. Upon re-hydration in DMEM or an appropriate buffer for collagen fiber self-assembly, the dextran template rapidly dissolved leaving behind networks of collagen fibers of the same geometry as the original fabric.

2-D Polyacrylamide Hydrogel Fabrication

Polyacrylamide hydrogels for immobilizing 2-D networks of collagen fibers were fabricated. Briefly, glass coverslips (22×22 mm) were placed on a 95° C. hotplate and covered with 500 µL 0.1N NaOH to activate the surface. The NaOH was evaporated and 500 µL of ddH$_2$0 was then applied and evaporated to improve the uniformity of the surface coating. The NaOH-coated coverslips were then treated with a 4% solution of (3-Aminopropyl)triethoxysilane in acetone for 15 min at room temperature. The resulting amine-functionalized coverslips were washed three times in ddH$_2$0 and air-dried. The coverslips were then exposed to a 0.8% solution of glutaraldehyde in PBS for 1 hour at room temperature. The coverslips were again washed three times in ddH$_2$0 and air-dried. Glutaraldehyde provided bi-functional cross-linking of the surface amines on the coverslips to the amide groups of the acrylamide-based hydrogels. To form uniform polyacrylamide hydrogels (shear modulus ~8.64) on the surface of the coverslips, solutions consisting of 7.5% acrylamide, 0.3% bis-acrylamide, 0.08% ammonium persulfate and 0.001% TEMED were sandwiched between the glutaraldehyde-coated coverslips (binding) and glass slides treated with trichlorosilane (release). After 30 minutes of polymerization, the coverslips containing polyacrylamide hydrogels were carefully removed from the slides and washed three times in ddH$_2$0. To provide sites for attachment of collagen fibers, the hydrogel surfaces were functionalized by incubation in a 2 mg/mL solution of sulfo-SANPAH under UV light for 5 minutes. The coverslips were washed five times in ddH$_2$0 and a final time in DMEM. Finally, the DMEM was completely removed and dry fabrics (10 layers thick) were applied to the surfaces to allow the collagen fibers to attach to the hydrogels. After 1 hour of incubation the hydrogels containing surface-bound collagen fibers were prepared for cell culture by incubation in growth medium.

3-D Agarose Hydrogel Fabrication

Agarose gels were formed by dissolving SeaPlaque™ Agarose (Lonza, Rockland, Me. USA) in serum-free culture medium to a concentration of 2 wt. % at temperatures above 70° C. The agarose solution was held at 37° C. in a water bath during cell preparation. An equal volume of warm cell suspension (20×10$^6$ cells/mL) and 2% agarose were mixed to achieve a final cell concentration of 10×10$^6$ cells/mL and a final agarose concentration of 1%. A volume of 75 µL of this mixture was immediately pipetted onto each ~15 mg dextran-fabric contained within separate wells of a 6-well culture plate. After 5 minutes of gelation, 2 mL of room temperature differentiation medium was added to each well.

Cell Culture

C2C12 mouse myoblasts (ATCC, CRL-1772) were cultured per ATCC instructions. Briefly, cells were cultured in growth medium consisting of DMEM containing 1% antibiotic antimycotic solution and 10% fetal bovine serum. Cells were passaged at ~50-60% confluence and used before 20 passages. For differentiation experiments, C2C12 cell were cultured in differentiation medium consisting of DMEM containing 1% antibiotic antimycotic solution, 2% fetal bovine serum, and 1% insulin, transferrin and selenium (ITS) solution. All cell cultures were maintained in a humidified incubator at 37° C. under 5% CO$_2$.

Immunolabeling, Staining and Microscopy

Antibodies to the native (helical form, C1A1 of Type I Collagen were used to label properly-assembled collagen structures. Antibodies to myosin heavy chain (Mouse-anti-Myosin-hc IgG, Novus Biologicals), NOS-I (Rabbit-anti-NOS-I IgG, Chemicon) and parvalbumin (Mouse-anti-Parvalbumin IgG, Chemicon) were used to assess C2C12 differentiation in 3-D culture conditions. HyLite 488-conjugated anti-mouse IgG and HyLite 555-conjugated anti-rabbit IgG secondary antibodies (Novus Biologicals, Oakville, ON Canada) were used for immunofluorescence detection as appropriate. Rhodamine-conjugated phalloidin was used to assess actin cytoskeleton organization for various culture conditions. Hoechst 33342 (Sigma Aldrich, St. Louis, Mo.), propidium iodide (Sigma) and Nuclear Green DCS1 (Abcam, Toronto, ON Canada) were used for nuclear counterstaining as indicated. Images were acquired using a Nikon Eclipse T1 epifluorescence microscope for 2-D cell cultures and low magnification images of 3-D cell cultures. A Zeiss LSM 510 Meta confocal system was used to acquire high resolution images of 3-D cell cultures. Stereomicroscopy was used to acquire images of dry fabrics. A Nikon polarizing microscope was used to acquire images of collagen fiber birefringence.

Aniline Blue Staining

Fomalin-fixed collagen networks were incubated in a solution of 2.5% phosphotungstic acid/2.5% phosphomolybdic acid in distilled water for 10 minutes. The collagen networks were then stained using a 2.5% solution of aniline blue in 1% acetic acid for 5 minutes. The collagen networks were rinsed in distilled water, cleared in 1% acetic acid, and rinsed again in distilled water before imaging by brightfield microscopy.

Image Analysis

Fiber density (number of fiber/ROI) and diameter of dry and hydrated collagen fabrics were determined by analyzing stereomicroscope images using Fiji. A 1.2 mm×1.2 mm region of interest (ROI) was selected at the center of each image. Wet and dry fiber diameters and density within the ROI were measured. Mean fiber density and diameter±the standard error of the mean were graphed as a function of collagen mass fraction.

For analysis of fiber orientation, threshold images of dry fabrics and C1A1 immunofluorescence were processed using the OrientationJ plugin for Fiji.

Example 6. Results

Figures 2A, 2B, 2C, 2D, 2E:
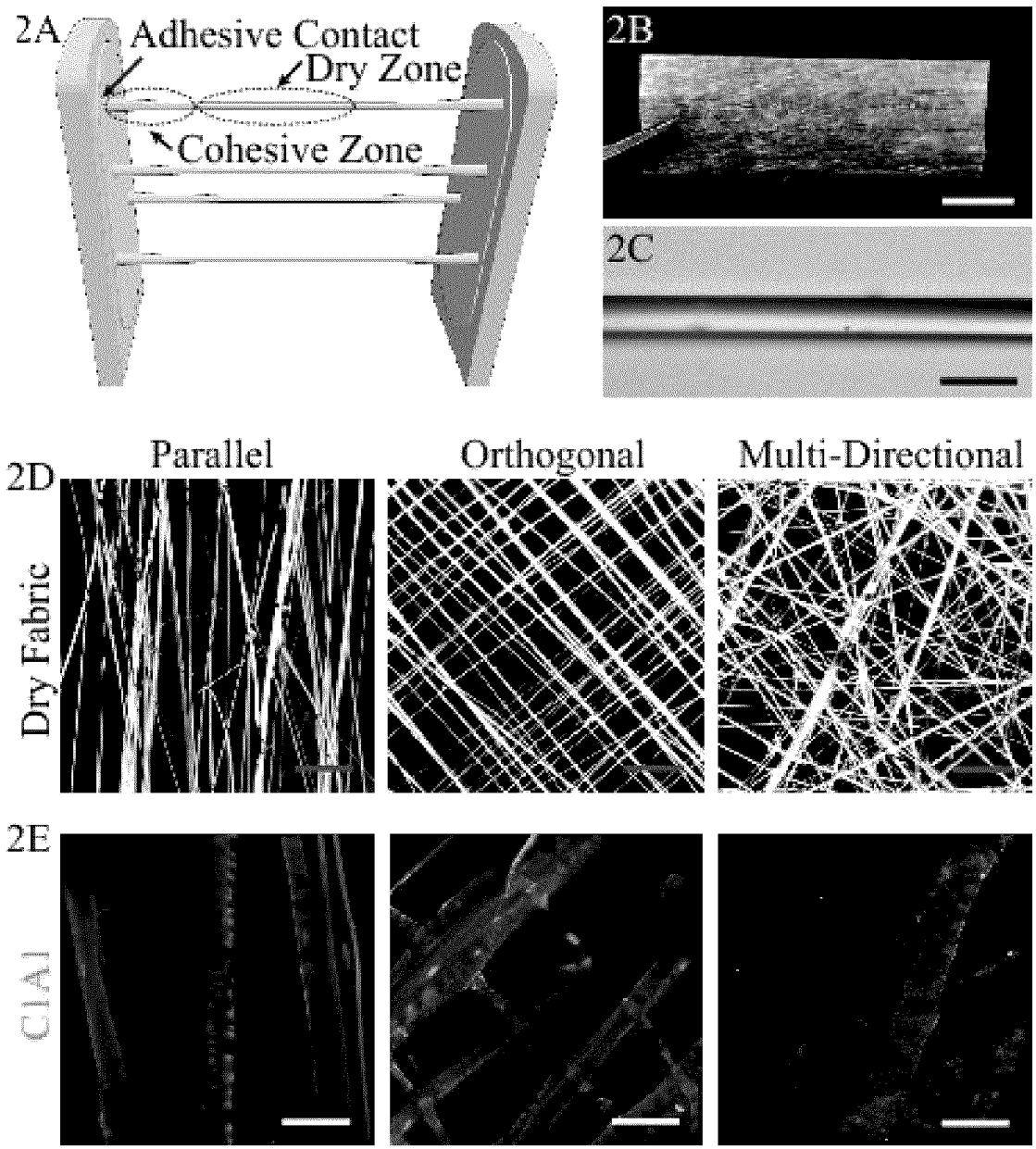
FIG. 2A depicts a diagrammatic representation of the CDP fiber synthesis. Two planar substrates brought into contact with a viscous solution of collagen-dextran polymer (CDP) composition can be used to elongate CDP fibers. Adhesive forces between the CDP solution and the substrates balance with cohesive forces to extend the CDP fibers as they dry in a central zone.
FIG. 2B is a photograph depicting dry CDP fabrics that are shelf-stable and can be easily manipulated for a variety of applications. CDP fabrics can also be trimmed to desired dimensions. Scale bar, 1 mm.
FIG. 2C depicts a single CDP fiber which is uniform and can be easily fabricated and collected. Shown is a region of a single CDP fiber imaged by brightfield microscopy. Scale bar, 50 μm.
FIG. 2D depicts darkfield stereomicroscopy images of exemplary CDP fabrics which can contain fibers in various interwoven configurations including parallel bundles, orthogonal lattices, and multi-directional lattice configurations. Scale bars, 500 μm.
FIG. 2E depicts immunofluorescence micrographs of CDP fibers after hydration in which dextran dissolves rapidly from CDP fabrics, leaving behind a network of collagen fibers corresponding to the dry template configuration. Immunofluorescence images for C1A1, an antibody that recognizes native helical collagen, demonstrate appropriate collagen self-assembly. Scale bars, 50 μm.

CDP fibers readily elongate as a viscous solution of 50% dextran and 50% collagen (wt/wt %) is pressed and pulled apart between two substrates, for example, two sterile tongue depressors (See FIG. 2A and FIG. 1A). CDP Fiber elongation is mediated by the balance of adhesive forces between the dextran solution and the two substrates and cohesive forces within the viscous dextran solution. CDP Fibers elongate from numerous points between the two substrates, allowing multiple fibers to be generated at once. CDP fibers rapidly dry as the CDP fibers elongate from viscous cohesive regions proximal to the two substrates, but remain flexible enough to apply them to a positionable stage without breakage. This allows multiple layers of CDP fibers to be applied to generate CDP fabrics that are several hundred layers thick (FIG. 2B). Individual elongated CDP fibers have a smooth, glass-like appearance and are typically between 10 and 100 µm in diameter (FIG. 2C). The positionable stage can be rotated between CDP fiber elongation cycles to generate CDP fabrics with various interwoven configurations, including CDP fabrics containing parallel CDP fibers, orthogonal interwoven CDP fibers and multi-directional interwoven CDP fibers (FIG. 2D). CDP fabrics stored dry under normal atmospheric conditions remain stable for several months without any noticeable loss of shape, fiber morphology or material properties.

Figures 3A, 3B:
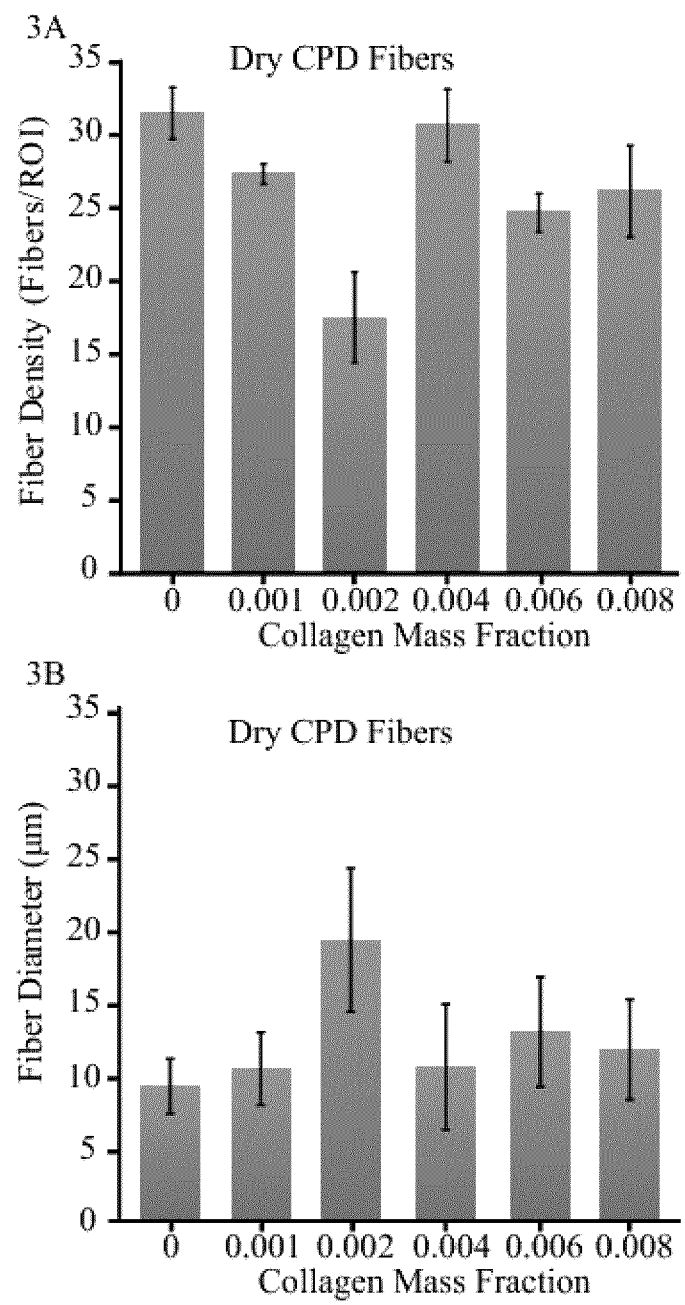
FIG. 3A depicts a bar graph comparing the fiber density versus the collagen mass fraction in the dry CDP fiber.
FIG. 3B depicts a bar graph comparing the fiber density versus the collagen mass fraction in the hydrated CDP fiber.
Figures 3C, 3D:
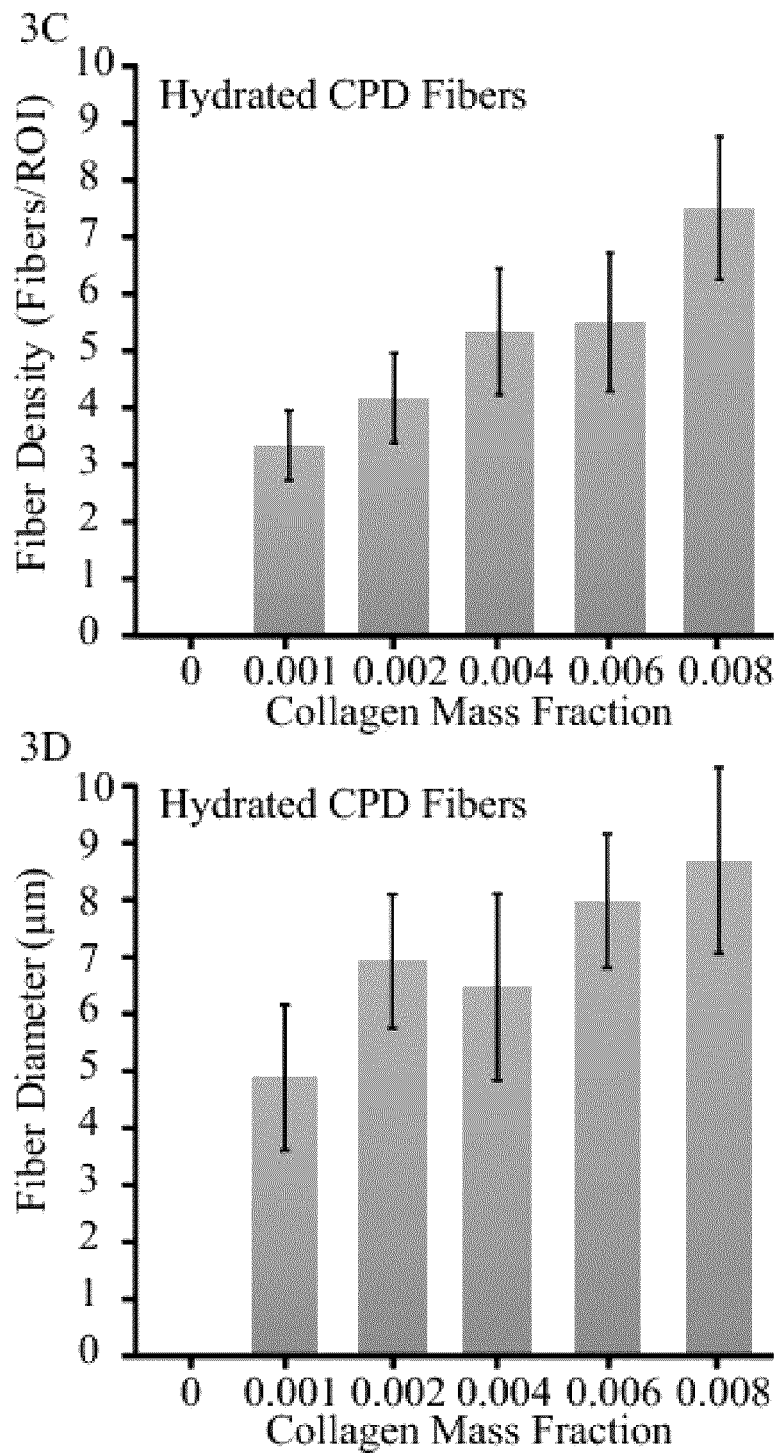
FIG. 3C depicts a bar graph comparing the fiber diameter (microns) versus the collagen mass fraction in the dry CDP fiber.
FIG. 3D depicts a bar graph comparing the fiber diameter (microns) versus the collagen mass fraction in the hydrated CDP fiber.
Figure 4:
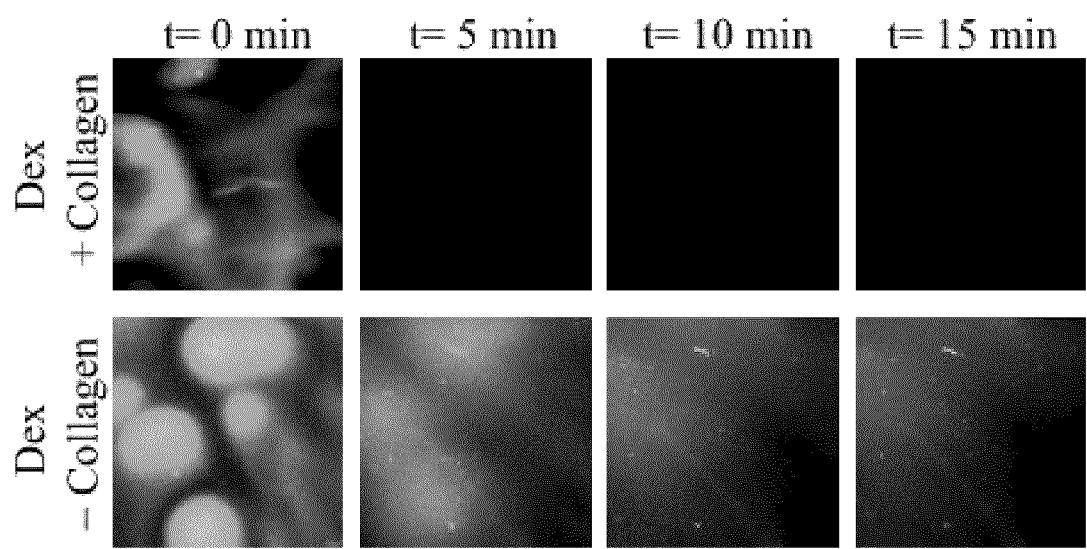
FIG. 4 depicts time lapsed photographs of light microscope images of dextran dissolution from CDP fibers in liquid.
Figure 5:
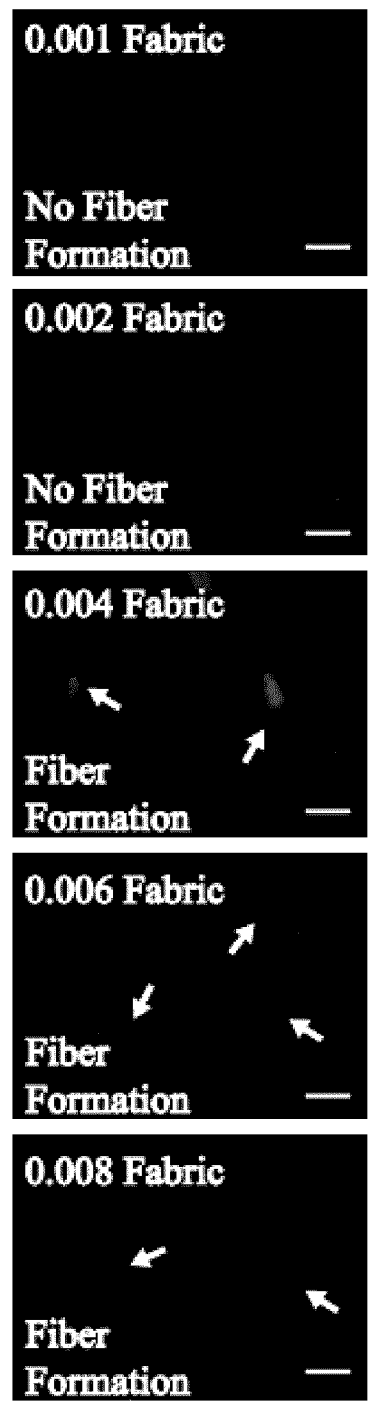
FIG. 5 depicts immunofluorescence micrographs demonstrating fibers containing mass fractions of collagen of 0.004 or greater form robust collagen fiber networks that display C1A1 immunofluorescence. Delicate fibers form sporadically for lower mass fractions of collagen. Scale, 20 μm.
Figure 6:
FIG. 6 depicts a photomicrograph image of representative collagen fiber birefringence. Fibers with different orientations display differential refractive characteristics when subjected to polarized illumination.
Figure 7:
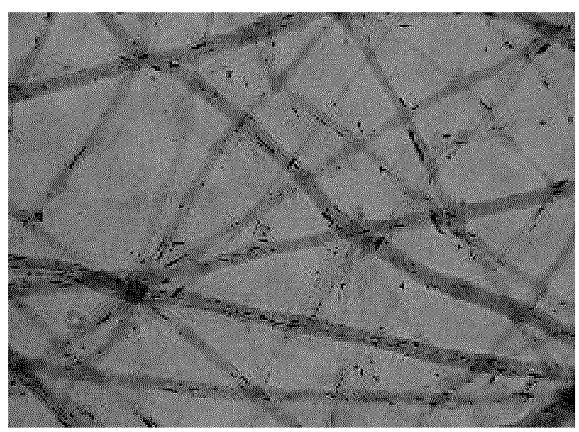
FIG. 7 depicts a photomicrograph image of a representative collagen fabric network stained with Masson's trichrome stain, including Aniline blue stain responsible for staining collagen, demonstrating that the collagen fibers formed following dextran dissolution in CDP fibers are highly enriched in collagen.

Incorporation of Type I collagen into the CDP composition has no significant influence on the fiber formation process, as indicated by comparison of dry fiber density (fibers/unit area) and fiber diameter for CDP fabrics and control fabrics (FIG. 3A-3B). However, both the density and diameter of collagen fibers present after rehydration increased with increasing collagen mass fraction (FIG. 3C-3D). Upon rehydration in an appropriate buffer for collagen fiber assembly, the dextran in the CDP fibers rapidly dissolves (FIG. 4), leaving behind a network of collagen fibers (FIG. 2E). CDP fabrics containing collagen: dextran mass fractions of 0.004 and above efficiently form collagen-rich fibers upon rehydration (FIG. 5). Most collagen fibers are between 5 and 20 µm in diameter, approximating the size scale of native collagen fibers observed in various tissues. These collagen fibers are recognized by antibodies to the native (helical, non-denatured) form of Type I collagen, suggesting that the fiber manufacturing process produces fibers containing collagen molecules with appropriate secondary protein structures. Collagen fibers produced by this process also display intrinsic birefringence when imaged by polarized light microscopy (FIG. 6). This crystalline-like optical behavior indicates ordering of collagen molecules parallel to the fiber axis, which is one of the hallmarks of properly assembled collagen fibers. In addition, collagen fibers stain strongly with aniline blue (FIG. 7), further suggesting that the structures that remain after dextran dissolution are primarily composed of collagen.

Figures 8A, 8B, 8C:
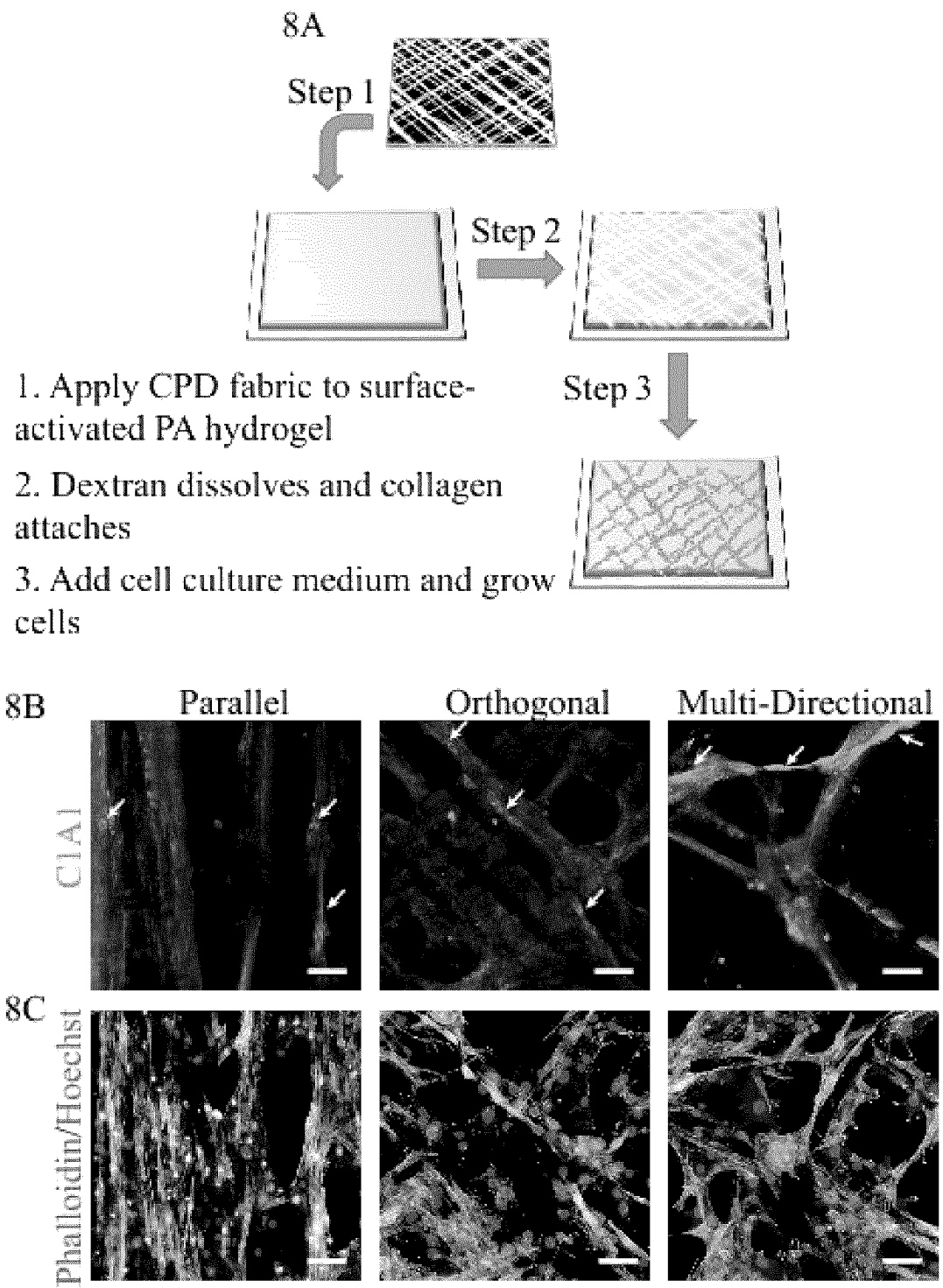
FIG. 8A depicts a schematic representation of the process for forming a 2-D and 3-D collagen fiber network construct in accordance with several embodiments of the present invention. In one embodiment, as shown in FIG. 8A collagen fabrics made in accordance with the present invention can be immobilized on the surface of polyacrylamide hydrogels to facilitate analysis of cell growth.
FIG. 8B depicts immunofluorescence photomicrographs of collagen networks shown remaining bound to the hydrogel surfaces following cell culture. Images shown are C1A1 immunofluorescence after 3 days in culture. Arrows indicate regions of additional cellular deposition of Type I collagen. All scale bars, 50 μm.
FIG. 8C depicts photomicrographs of collagen networks stained with Actin-phalloidin and Hoechst nuclear staining of cells growing along the collagen fiber networks shown in (FIG. 8B). All scale bars, 50 μm.
Figures 9A, 9B:
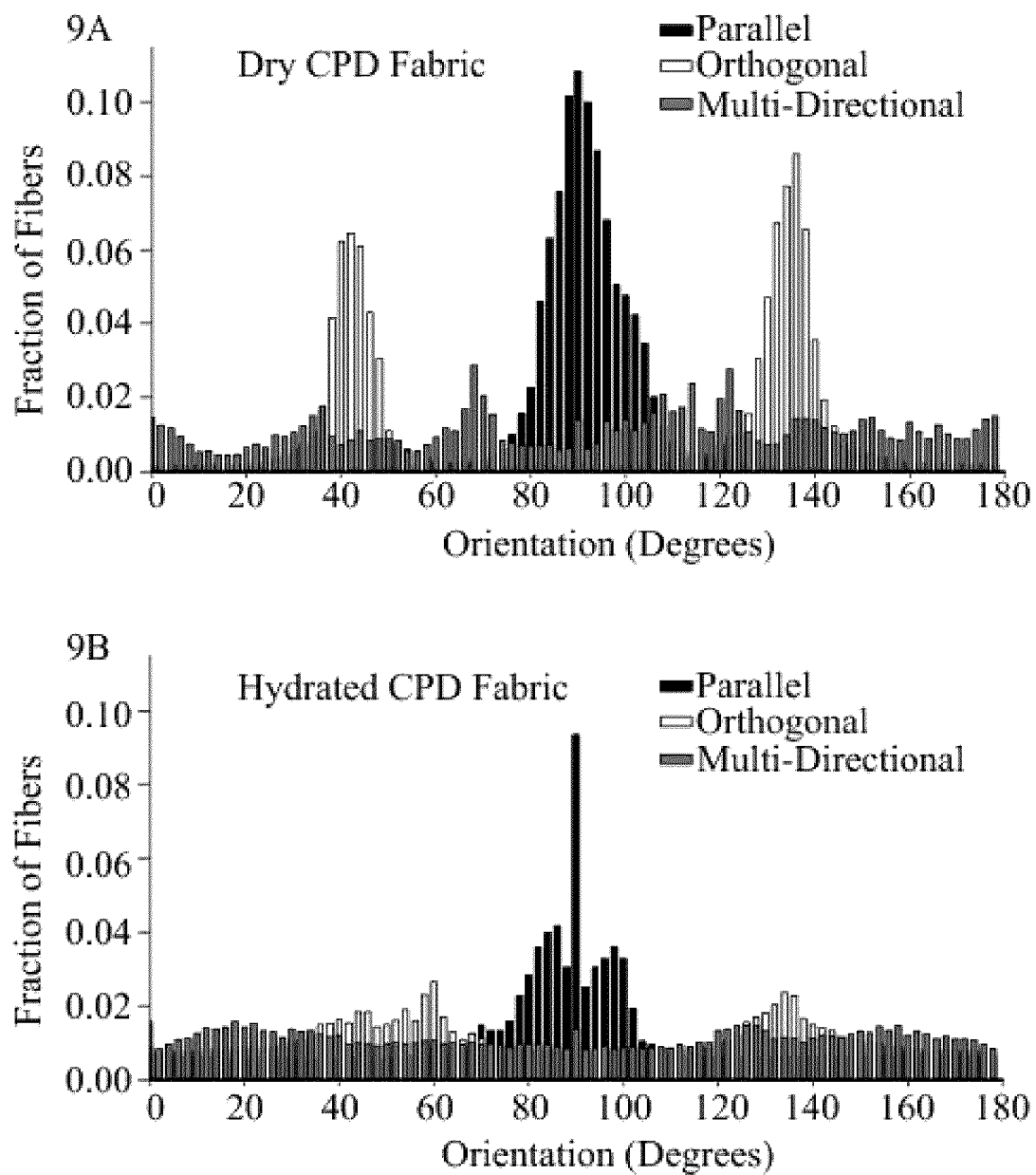
FIG. 9A depicts a histogram of the fraction of fibers versus the orientation of fibers (parallel, orthogonal and multi-directional) when dried.
FIG. 9B depicts a histogram of the fraction of fibers versus the orientation of fibers (parallel, orthogonal and multi-directional) when hydrated.

The collagen fibers produced by this manufacturing process can be used as a surface-anchored biomaterial network capable of directing growth of C2C12 myoblasts (FIG. 8A). Attaching the collagen fibers as a 2-D network to the surface of a non-adherent polyacrylamide hydrogel facilitates observation of C2C12 attachment, alignment and growth. Collagen fibers bound to the surface of non-adherent polyacrylamide hydrogels retain their woven configurations in culture (FIG. 8B and FIGS. 9A-9B). Over a 3-day period of cell culture, C2C12 cells selectively attach and grow along the fibers as indicated by actin-phalloidin staining and Hoechst nuclear staining (FIG. 8C), forming fascicle-like structures. Inspection of cell growth patterns indicates that both the cells and the actin cytoskeleton within the cells align with the collagen network. In addition, undifferentiated C2C12 cells gradually remodel the collagen network by displacing collagen fibers through traction force and by synthesizing and secreting additional Type I collagen along existing fibers (arrows in FIG. 8B).

Figures 10A, 10B, 10C, 10D:
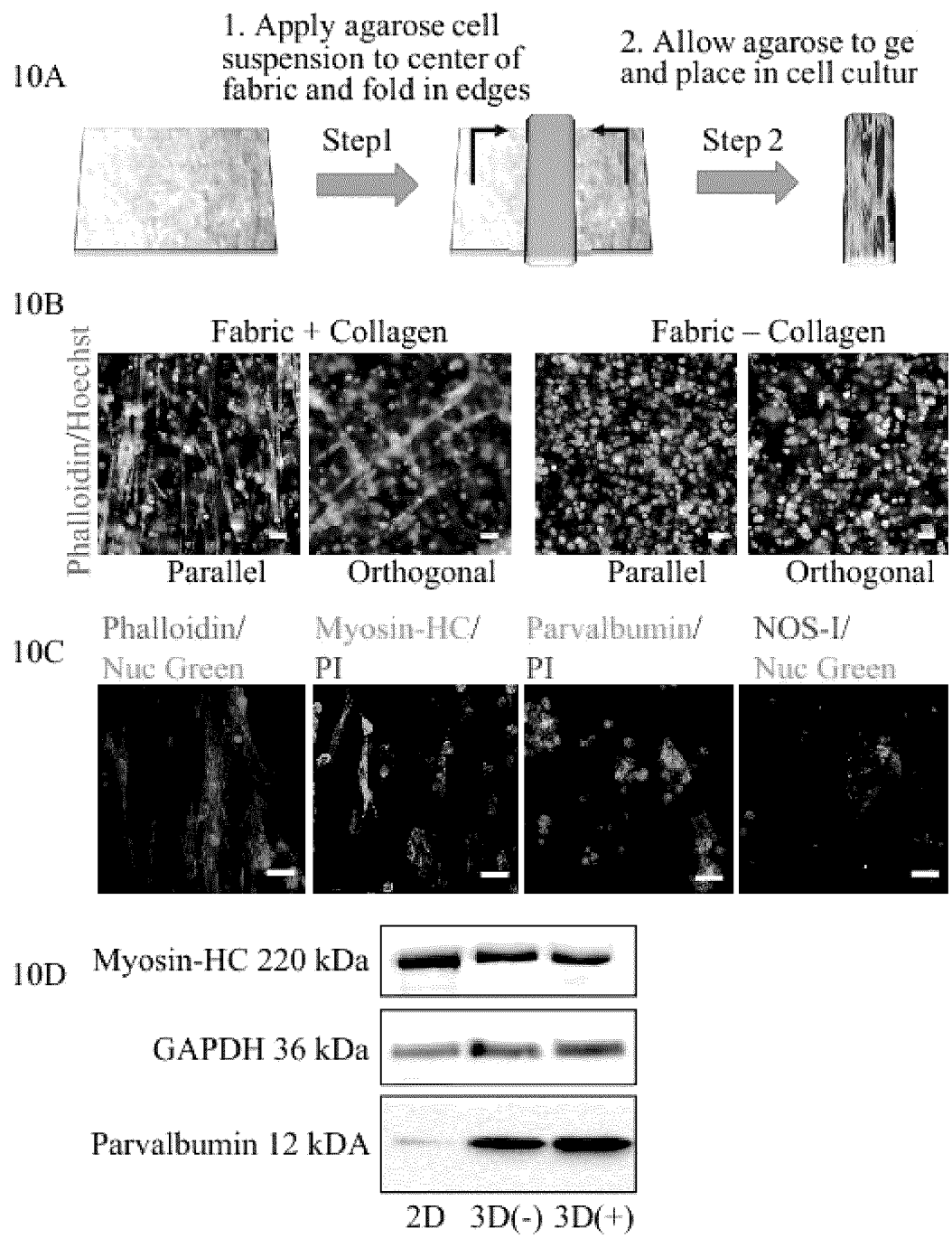
FIG. 10A depicts a schematic representation for the synthesis of a 3-D collagen fiber network construct in accordance with several embodiments of the present invention. All scale bars, 50 μm.
FIG. 10B depicts photomicrographs epifluorescence images of actin-phalloidin and Hoechst nuclear staining of CDP fabric and dextran fabric (with and without collagen) demonstrating that CDP fabrics promote large scale alignment of agarose-encapsulated C2C12 cells. Cell alignment and growth is not observed for control dextran fabrics that do not contain collagen. All scale bars, 50 μm.
FIG. 10C depicts photomicrographs of high-resolution confocal maximum intensity projection images showing details of aligned fascicle-like structures in CDP fabrics. Positioning of cell nuclei and interconnected cytoskeleton structures are indicative of myotube formation. Myotubes and fascicle-like structures are not observed for cells cultured with control dextran fabrics (without collagen). All scale bars, 50 μm.
FIG. 10D depicts photomicrographs of Western blots performed on lysates from C2C12 cells growing along collagen containing collagen networks prepared from CDP fabrics. Skeletal muscle cell differentiation markers including myosin heavy chain and parvalbumin are observed.

CDP fabrics are also capable of aligning cells grown under 3-D cell culture (FIG. 10A). After 7-10 days of 3-D cell culture in low gelling point agarose hydrogels containing CDP fabrics aligned in a single direction, many elongated cells are evident by actin-phalloidin staining (FIG. 10B). In contrast, cells growing in agarose surrounding control fabrics (no collagen) remain clustered in spherical structures, indicating a lack of cell attachment and growth within the hydrogel. High-resolution confocal imaging indicates that aligned structures form from cells growing in continuous chain-like structures, indicating the potential for myotube formation as the cells differentiate (FIG. 10C). Myotube-like structures were not observed in agarose hydrogels containing control fabrics without collagen. Many of the aligned cells displayed markers of differentiated skeletal muscle, as indicated by Western blot analysis of cells growing on collagen fibers for myosin heavy chain (a motor protein found in skeletal muscle thick filaments) and parvalbumin (a high-affinity $Ca^{2+}$-binding protein found in fast-contracting skeletal muscle fibers) (FIG. 10D). Collectively, these results demonstrate that the described method for forming 3-D collagen networks can support the growth and differentiation of skeletal muscle cells within non-cell-adherent hydrogels.

Figure 11A:
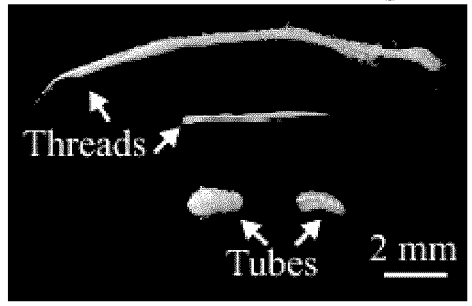
FIG. 11A shows photographs of threads and tubes formed from CPD fibers.
Figure 11B:
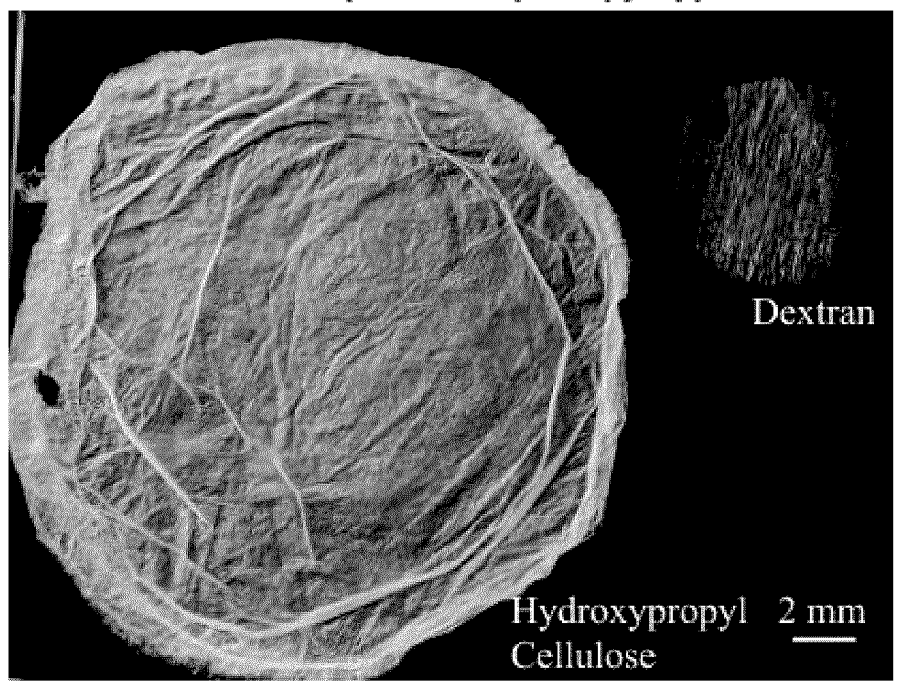
FIG. 11B shows photographs of circular fabrics of different sizes formed from hydroxypropyl cellulose and dextran.

Further proof-of-concept for manufacturing ensembles of fibers of various shapes (FIG. 11A) and sizes (FIG. 11B) demonstrate the versatily of this approach for producing fabrics for a wide variety of applications in the realm of biomaterials and other fields of application.

Example 7. Discussion

Using C2C12 cells, which are a well-established model cell line for understanding skeletal muscle development and physiology, we demonstrate production and application of a novel collagen-based biomaterial capable of organizing muscle cells into fascicle-like structures. In muscle tissue, fascicles are present in various patterns, giving rise to unique force generation properties within the tissue. Within each fascicle, groups of muscle cells are organized by collagen fibers, which can extend along or across muscle cells, before eventually inserting into tendons. The novel collagen-based biomaterial characterized in this study is especially well suited for fabricating tissue models that display this pattern of collagen fiber and cell alignment.

One of the most attractive features of the dextran-collagen material is that it allows cells encapsulated within hydrogels to elongate and grow into networks. This is one of the most challenging aspects of 3-D cell culture that limits the applicability of many hydrogel systems as in vitro models and as materials for regenerative medicine. In addition to myotube formation in skeletal muscle, various other cell types such as neural cells and vascular cells depend on network formation for appropriate physiological function. Since collagen has been demonstrated to support the growth of these cell types and many other cell types, this approach may prove beneficial to constructing many different types of model tissues. Moreover, since the collagen network produced by the manufacturing process is a free-standing structure, it is highly versatile and can be applied to functionalize many other types of hydrogel scaffolds and surfaces, e.g., other non-adherent hydrogels such as alginate or polyethylene glycol diacrylate. Here, we demonstrate that it can be used to support highly-specific myoblast growth with two types of non-cell-adherent hydrogels (i.e., poly-acrylamide and agarose), but it is possible that this material can be used to generate large scale networks of organized skeletal muscle cells within other types of natural and synthetic biomaterials for modeling musculoskeletal disease and use in wound reconstruction.

The collagen-doped dextran fabrics could potentially be applied for shaping and applying these composite materials. Bioactive agents could also be included in these constructs, which would allow for controlled elution of useful drugs and/or biomolecules, in addition to delivery of a collagen matrix to augment cell attachment, alignment and growth. While here the focus is mainly on generating pure collagen biomaterials to functionalize 2-D and 3-D cell culture substrates, drug-eluting dextran fabrics could be combined with these most recent findings to address wound healing applications. For example, dextran fabrics containing thrombin and antibiotics effectively promoted coagulation of human platelet poor plasma and suppressed bacterial growth in vitro. The addition of collagen fibers could further promote endothelial migration, fibroblast proliferation and platelet aggregation to enhance wound healing with this material.

In terms of manufacturing, one of the strength of this collagen fiber formation process is that it only requires simple motions to form elongated fibers. Thus, the overall procedure can be adapted to an automated manufacturing system to further improve throughput and consistency. For example, programmed volumes of collagen-doped dextran could be extruded onto two flat arms. Pressing and releasing the two arms to a set distance along the y-axis would induce fiber formation. As the fibers form, the arms could then travel down the z-axis towards a collector where the fibers would be deposited. A turning motion of the collector with a partial lip on both ends could then clip the ends of the fibers, and the arms would return to their initial positioning, where additional collagen-doped dextran could be added and the process repeated for a predetermined number of layers. Fiber orientation could be controlled with programmed turns of the collector to generate consistently organized fabrics with defined fiber directions. An automated manufacturing scheme such as this, utilizing standard robotic designs and simple movements, would enable mass manufacturing of dextran materials for healthcare applications. An additional strength of this approach is that it utilizes only a few reagents that are already produced in cGMP facilities and are readily available as pharmaceutical grade preparations, although it will be possible to design fibers for specific indications through use of formulations comprising other polymers listed in TABLE 1, cross-linking of the polymers or employing blends of polymers.

In conclusion, an entirely new process for fabricating collagen fibers of appropriate size scales for promoting interaction with cells is presented. The fibers produced by this manufacturing process can be aligned in several configurations and that the collagen from which the fibers are formed displays the appropriate molecular organization (e.g., intact α-helical structure and birefringence). It is also demonstrated that myoblasts readily attach and align along 2-D collagen fiber networks. Furthermore, encapsulation of collagen fibers with cells into non-cell-adherent hydrogels promotes aligned growth of cells and supports their differentiation. The ease-of-production and versatility of this novel collagen-based biomaterial will support future development of a variety of tissue-engineered disease models and materials for regenerative medicine and wound reconstruction. Furthermore, it appears from preliminary studies that the ability of cells to attach and grow on the fibers does not degrade with fabric age. No differences in cell attachment have been observed between freshly prepared fabrics and fabrics stored at room temperature for several months.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the claims.

What is claimed is:

1. A biomaterial fabrication process for the manufacture of a collagen based fabric for an aligned collagen fiber network, the process comprising:
   a. providing a collagen-polymer composition comprising collagen and a polymer;
   b. applying the collagen-polymer composition to a first surface of a first substrate;
   c. contacting the collagen-polymer composition with a first surface of a second substrate, thereby interposing the collagen-polymer composition between the first substrate and the second substrate;
   d. forming a plurality of elongated collagen-polymer fibers by pressing and separating the first and second substrates along an axis thereby elongating the collagen-polymer composition and forming the plurality of elongated collagen-polymer fibers; and,
   e. placing the elongated collagen-polymer fibers onto a stage thereby forming a collagen-polymer fiber layer or collagen-polymer fabric of collected collagen-polymer fibers.

2. The biomaterial fabrication process according to claim 1, wherein the polymer is dextran, hydroxypropyl cellulose, poly(2-ethyl-2-oxazoline), poly(4-styrenesulfonic acid-co-maleic acid), poly(acrylic acid), poly(diallyldimethyl ammonium chloride), poly(methacrylic acid), poly(methyl vinyl ether-alt-maleic acid), poly(vinyl alcohol) or poly (vinylpyrrolidone).

3. The biomaterial fabrication process according to claim 1, wherein:
   the collagen-polymer composition is a collagen-dextran polymer (CDP) composition;
   the elongated collagen-polymer fibers are elongated CDP fibers;
   the collagen-polymer fiber layer is a CDP fiber layer; and,
   the collagen-polymer fabric of collected collagen-polymer fibers is a CDP fabric of collected CDP fibers.

4. The biomaterial fabrication process according to claim 3, wherein the ratio of collagen to dextran in the CDP composition ranges from about 0.1% to about 1.57% collagen to about 99.9% to about 98.43% dextran.

5. The biomaterial fabrication process according to claim 4, wherein the ratio of collagen to dextran in the CDP composition ranges from about 0.2% to about 0.79% collagen to about 99.8% to about 99.21% dextran.

6. The biomaterial fabrication process according to claim 3, wherein the collagen is Type I collagen.

7. The biomaterial fabrication process according to claim 3, wherein the CDP composition has a collagen:dextran mass fraction ranging from 0.004 to 0.008.

8. The biomaterial fabrication process according to claim 3, wherein the CDP composition at 22° C. has a viscosity ranging from about 15,000 centipoise to about 100,000 centipoise as measured by the vertical falling ball method.

9. The biomaterial fabrication process according to claim 3, wherein the elongated CDP fibers have a diameter ranging from about 0.1 μm to about 500 μm.

10. The biomaterial fabrication process according to claim 9, wherein the elongated CDP fibers have a diameter ranging from about 1 μm to about 100 μm.

11. The biomaterial fabrication process according to claim 3, wherein the elongated CDP fibers in the CDP fiber layer or CDP fabric are arranged in parallel, in orthogonal)(90°) or in multi-directional orientation.

12. The biomaterial fabrication process according to claim 3, wherein the process further comprises contacting the CDP fiber layer or CDP fabric with a solvent to dissolve the dextran in the CDP fiber layer or CDP fabric.

13. The biomaterial fabrication process according to claim 12, wherein the solvent to dissolve the dextran in the CDP fiber layer or CDP fabric comprises an aqueous solution.

14. The biomaterial fabrication process according to claim 13, wherein the aqueous solution comprises water, 0.9% NaCl physiological saline, 50 mM Tris, 150 mM NaCl Tris-buffered saline, lactated Ringer's solution, Ringer-acetate solution, tissue culture media, or combinations thereof.

* * * * *